United States Patent [19]
Lal et al.

[11] Patent Number: 6,165,767
[45] Date of Patent: Dec. 26, 2000

[54] PROTEIN PHOSPHATASE-RELATED MOLECULES

[75] Inventors: Preeti Lal, Santa Clara; Henry Yue, Sunnyvale; Neil C. Corley, Mountain View; Karl J. Guegler, Menlo Park; Mariah Baughn, San Jose, all of Calif.

[73] Assignee: Incyte Pharmaceuticals, Inc., Palo Alto, Calif.

[21] Appl. No.: 09/045,973

[22] Filed: Mar. 20, 1998

[51] Int. Cl.⁷ .................................................. C12N 9/14
[52] U.S. Cl. .......................... 435/196; 435/6; 435/69.1; 435/252.3; 435/320.1; 536/23.2; 536/23.5
[58] Field of Search .............................. 435/196, 6, 69.1, 435/320.1, 252.3, 325; 536/23.2, 23.5

[56] References Cited

PUBLICATIONS

NCI–CGAP, Genbank Sequence Database. (Accession # AA573790) National Center for Biotechnology Information, National Library of Medicine, Bethesda MD 20894, Sep. 1997.

Hillier et al. Genbank Sequence Database. (Accession # AA081740) National Center for Biotechnology Information, National Library of Medicine, Bethesda MD 20894, Dec. 1997.

Hillier et al. Genbank Sequence Database. (Accession # AA404288) National Center for Biotechnology Informataion, National Library of Medicine, Bethesda MD 20894, May 1997.

Hillier et al. Genbank Sequence Database. (Accession # AA165047) National Center for Biotechnology Information, National Library of Medicine, Bethesda MD 20894, Dec. 1996.

Adams et al. Genbank Sequence Database. (Accession # AA307000) National Center for Biotechnology Information, National Library of Medicine, Bethesda MD 20894, Apr. 1997.

Scanlan et al. Characterization of Human Colon Cancer Antigens Recognized By Autologous Antibodies. Int. J. Cancer. 76:652–658, May 29, 1999.

Hillier et al. Genbank Sequence Database. (Accession # AA156751) National Center for Biotechnology Information, National Library of Medicine, Bethesda MD 20894, Dec. 1996.

Adams et al. Genbank Sequence Database. (Accession # Q60738) National Center for Biotechnology Information, National Library of Medicine, Bethesda MD 20894, Feb. 1993.

Hudson, T. Genbank Sequence Database. (Accession # G26291) National Center for Biotechnology Information, National Library of Medicine, Bethesda MD 20894, May 1996.

Hillier et al. Genbank Sequence Database. (Accession # AA126103) National Center for Biotechnology Information, National Library of Medicine, Bethesda MD 20894, Nov. 1996.

Hillier et al. Genbank Sequence Database. (Accession # W30715) National Center for Biotechnology Information, National Library of Medicine, Bethesda MD 20894, Aug. 1996.

Birren et al. Genbank Sequence Database. (Accession # AC004099) National Center for Biotechnology Information, National Library of Medicine, Bethesda MD 20894, Feb. 1, 1998.

Cohen, P., "The Structure and Regulation of Protein Phosphatases," *Annu. Rev. Biochem.*, 58:453–508 (1989).

Charbonneau, H. and Tonks, N.K., "1002 Protein Phosphatases?" *Annu. Rev. Cell Biol.*, 8:463–493 (1992).

Sadhu, K. et al., "Human homolog of fission yeast cdc25 mitotic inducer is predominantly expressed in $G_2$," *Proc. Natl. Acad. Sci. USA*, 87:5139–5143 (1990).

Balakrishnan, R. et al., (GI 392019, GI 401712), GenBank Sequence Database (Accession U00148), National Center for Biotechnology Information, National Library of Medicine, Bethesda, Maryland 20894 (Dec. 1993).

Balakrishnan, R. et al., "Appendix: Cloning and Sequence of the Gene Encoding Enzyme E–1 from the Methionine Salvage Pathway of *Klebsiella Oxytoca*," *J. Biol. Chem.*, 268(33):24792–24795 (1993).

Wilson, R. et al., (GI 1495336, GI 1495338), GenBank Sequence Database (Accession Z78419), National Center for Biotechnology Information, National Library of Medicine, Bethesda, Maryland 20894 (Jan. 1998).

Chinkers, M., ( GI 567039, GI 567040), GenBank Sequence Database (Accession U12204), National Center for Biotechnology Information National Library of Medicine, Bethesda, Maryland 20894 (Nov. 1996).

Chinkers, M., "Targeting of a distinctive protein–serine phosphatase to the protein kinase–like domain of the atrial natriuretic peptide receptor," *Proc. Natl. Acad. Sci. USA*, 91:11075–11079 (1994).

*Primary Examiner*—Rebecca E. Prouty
*Assistant Examiner*—Richard Hutson
*Attorney, Agent, or Firm*—Incyte Pharmaceuticals, Inc.

[57] ABSTRACT

The invention provides human protein phosphatase-related molecules (PPRM) and polynucleotides which identify and encode PPRM. The invention also provides expression vectors, host cells, antibodies, agonists, and antagonists. The invention also provides methods for diagnosing, treating or preventing disorders associated with expression of PPRM.

12 Claims, 18 Drawing Sheets

```
5' ATC GCG GGC  TCG GGC TGC  GGG GCT CCG  GCT GCG CCG  CGA GGC GCG
         9           18           27           36           45           54

GAG CTT GGG  AGC GGA GCC  CAG GCC GTG  CCG AAG GGC  AAG GAG
     63           72           81           90           99          108
                                              M    K    G    K    E

GAG AAG GGC  GGC GGC GCA  CGG CTG GGC  GCT GGC AGC  GGA AGC CCC  GAG AAG AGC
    117          126          135          144          153          162
 E    K    G    A    R    L    G    A    G    S    G    S    P    E    K    S

CCG AGC GCG  CAG GAG CTC  AAG GAG GAG  CAG GGC AAT  CGT CTG TTC  GTG GGC CGA AAG
    171          180          189          198          207          216
 P    S    A    Q    E    L    K    E    E    Q    G    N    R    L    F    V    G    R    K

TAC CCG GAG  GCG GCG GCG  GCC TGC TAC  CGC GCG ATC  ACC CGG AAC  CCG CTG GTG
    225          234          243          252          261          270
 Y    P    E    A    A    A    C    Y    R    A    I    T    R    N    P    L    V

GCC GTG TAT  TAC ACC AAC  CGG GCC TTG  TGC TAC CTG  AAG ATG CAG  CAG CAC GAG
    279          288          297          306          315          324
 A    V    Y    Y    T    N    R    A    L    C    Y    L    K    M    Q    Q    H    E

CAG GCC CTG  GCC GAC TGC  CGG CGC GCC  CTG GAG CTG  GAC GGG CAG  TCT GTG AAG
    333          342          351          360          369          378
 Q    A    L    A    D    C    R    R    A    L    E    L    D    G    Q    S    V    K
```

FIGURE 1A

```
387 GCG CAC TTC CTG  396 GGG CAG TGC  405 CAG CTG GAG  414 ATG GAG AGC  423 TAT GAT GAG  432 GCC
     A   H   F   L        G   Q   C        Q   L   E        M   E   S        Y   D   E        A

441 ATC GCC AAT CTG  450 CAG CGA GCT  459 TAC AGC CTG  468 GCC AAG CAG  477 CGG CTG AAC  486 TTC
     I   A   N   L        Q   R   A        Y   S   L        A   K   Q        R   L   N        F

495 GGG GAC GAC ATC  504 CCC AGC GCT  513 CTT CGA ATC  522 GCG AAG AAG  531 CGC TGG AAC  540 AGC
     G   D   D   I        P   S   A        L   R   I        A   K   K        R   W   N        S

549 ATT GAG GAG CGG  558 CGC ATC CAC  567 CAG GAG AGC  576 CTG GAA GAG  585 TAC CTC TCC  594 AGG
     I   E   E   R        R   I   H        Q   E   S        L   E   E        Y   L   S        R

603 CTC ATT GCC GCG  612 GAG CGT GAG  621 AGG GAG CTG  630 GAG GAG CTG  639 CGA AAC CAC  648 GAG
     L   I   A   A        E   R   E        R   E   L        E   E   L        R   N   H        E

657 GAG GAG GAC GAC  666 AGC CAC GTC  675 CGG GCC CAG  684 GCC CAG TGC  693 ATT GAG GCC  702 AAG
     E   E   D   D        S   H   V        R   A   Q        A   Q   C        I   E   A        K

711 CAC AAG TAC ATG  720 GCG GAC ATG  729 GAC GAG CTT  738 TTT TCT CAG  747 GTG GAT GAG  756 AAG
     H   D   K   Y   M    A   D   M        D   E   L        F   S   Q        V   D   E        K
```

FIGURE 1B

```
AGG AAG CGA GAC ATC CCC GAC TAC CTG TGT AAG ATC AGC TTT GAG CTG
 R   K   R   D   I   P   D   Y   L   C   K   I   S   F   E   L
765             774             783             792     801     810

ATG CGG GAG CCG TGC ATC ACG CCC AGT GGC ATC ACC TAC GAC AAG GAC ATC
 M   R   E   P   C   I   T   P   S   G   I   T   Y   D   K   D   I
819             828             837             846     855     864

GAG GAG CAC CTG CAG CGT GTG GGT CAT TTT GAC CCC GTG ACC CGG AGC CCC CTG
 E   E   H   L   Q   R   V   G   H   F   D   P   V   T   R   S   P   L
873             882             891             900     909     918

ACC CAG GAA CAG CTC ATC CCC AAC TTG GCT ATG AAG GAG GTT ATT GAC GCA TTC
 T   Q   E   Q   L   I   P   N   L   A   M   K   E   V   I   D   A   F
927             936             945             954     963     972

ATC TCT GAG AAT GGC TGG GTG GAG GAC TAC TGA GGT TCC CTG CCC TAC CTG GCG
 I   S   E   N   G   W   V   E   D   Y   *
981             990             999             1008    1017    1026

TCC TGG TCC AGG GGA GCC CTG GGC AGA AGC CCC CGG CCC CTA TAC ATA GTT TAT
1035            1044            1053            1062    1071    1080
```

FIGURE 1C

```
     1089            1098            1107            1116            1125            1134
GTT CCT GGC CAC CCC GAC CGC TTC CCC CAA GTT CTG CTG TTG GAC TCT GGA CTG 1143            1152            1161            1170            1179            1188
TTT CCC CTC TCA GCA TCG CTT TTG CTG GGC CGT GAT CGT CCC CCT TTG TGG GCT 1197            1206            1215            1224            1233            1242
GGA AAA GCA GGT GAG GGT GGG CTG TGA GGC CAC GAG TGC CAC TAT CTG TGT 1251            1260            1269            1278            1287            1296
AAT AAA ATC CGT GAG CAC GAG GGA CGT GCT GGT GTG TGA CCG GCA GTC CTG 1305            1314            1323            1332
CCA GCT GTT TTG GCT AGC CGA GGA AGG TGG AGA TGA AGA       3'
```

FIGURE 1D

```
                        10            19            28         37            46            55
5' GGGC GGC CGC CTT TTC CAG TTC CAG GTG TGC AGA AGT GTC CTC TCC CCA CGC GCG 64            73            82         91           100           109
   GCG GGC TGC ACT TGG TCG CTG GCT CCG AGA TCG CGC GGG GCC GCC GGA AGC CCA 118           127           136        145           154           163
   AGA CGG TAC CGG CCG CAG CCG CAG CCG GCG CCG CCC TCC GCC CTC CCC AAC 172           181           190        199           208           217
   AGC AGG CCG AGT CCC GTA GCA TCC GGT AGG GAA ATG GTC GTG CTT TCG GTC CCC
                                                    M   V   V   L   S   V   P 226           235           244        253           262           271
   GCC GAA GTC ACC GTG ATC CTG TTA GAT ATC GAA GGT ACC ACA CCG ATT GCT
    A   E   V   T   V   I   L   L   D   I   E   G   T   T   P   I   A 280           289           298        307           316           325
   TTC GTG AAG GAC ATT TTA TTT CCT TAC ATC GAA GAA AAT GTT AAA GAG TAT CTG
    F   V   K   D   I   L   F   P   Y   I   E   E   N   V   K   E   Y   L 334           343           352        361           370           379
   CAG ACA CAT TGG GAA GAA GAG GAG TGC CAG CAG GAT GTC AGT CTT TTG AGG AAA
    Q   T   H   W   E   E   E   E   C   Q   Q   D   V   S   L   L   R   K

FIGURE2A
```

| | | | | | | | 433 |
|---|---|---|---|---|---|---|---|
| | 388 | 397 | 406 | 415 | 424 | | |
| CAG | GCT | GAA | GAG | GAC | GCC | CAC | CTG | GAT | GGG | GCT | GTT | CCT | ATC | CCT | GCA | GCA | TCT |
| Q | A | E | E | D | A | H | L | D | G | A | V | P | I | P | A | A | S |

| | 442 | 451 | 460 | 469 | 478 | | 487 |
|---|---|---|---|---|---|---|---|
| GGG | AAT | GGA | GTG | GAT | CTG | CAA | CAG | ATG | ATC | CAG | GCC | GTG | GTA | GAT | AAT | GTG |
| G | N | G | V | D | L | Q | Q | M | I | Q | A | V | V | D | N | V |

| | 496 | 505 | 514 | 523 | 532 | | 541 |
|---|---|---|---|---|---|---|---|
| TGC | TGG | CAG | ATG | TCC | CTG | GAT | CGA | AAG | ACC | ACT | GCA | CTC | AAA | CAG | CTG | CAG | GGC |
| C | W | Q | M | S | L | D | R | K | T | T | A | L | K | Q | L | Q | G |

| | 550 | 559 | 568 | 577 | 586 | | 595 |
|---|---|---|---|---|---|---|---|
| CAC | ATG | AGG | GCG | GCA | TTC | ACA | GCT | GGG | CGC | ATG | AAA | GCA | GAG | TTC | TTT | GCA |
| H | M | R | A | A | F | T | A | G | R | M | K | A | E | F | F | A |

| | 604 | 613 | 622 | 631 | 640 | | 649 |
|---|---|---|---|---|---|---|---|
| GAT | GTA | GTT | CCA | GCA | GTC | AGG | AAG | TGG | AGA | GAG | GCA | ATG | GCC | GGA | ATG | AAG | GTG | TAC | ATC |
| D | V | V | P | A | V | R | K | W | R | E | A | M | A | G | M | K | V | Y | I |

| | 658 | 667 | 676 | 685 | 694 | | 703 |
|---|---|---|---|---|---|---|---|
| TAT | TCC | TCA | GGG | AGT | GTG | GAG | GCA | CAG | AAA | CTG | TTA | TTC | GGG | CAT | TCT | ACG | GAG |
| Y | S | S | G | S | V | E | A | Q | K | L | L | F | G | H | S | T | E |

| | 712 | 721 | 730 | 739 | 748 | | 757 |
|---|---|---|---|---|---|---|---|
| GGA | GAT | ATT | CTT | GAG | CTT | GTT | GAT | GGT | CAC | TTT | GAT | ACC | AAG | ATT | GGA | CAC | AAA |
| G | D | I | L | E | L | V | D | G | H | F | D | T | K | I | G | H | K |

FIGURE 2B

```
                                                                        811              865              919              973             1027             1081             1135
     766      775      784      793      802                    820      829      838      847      856                    874      883      892      901      910                    928      937      946      955      964                    982      991     1000     1009     1018                   1036     1045     1054     1063     1072                   1090     1099     1108     1117     1126
GTA GAG AGT GAA AGT TAC CGA AAG ATT GCA GAC AGC ATT GGG TGC TCA ACC AAC     AAC ATT TTG TTT CTG ACA GAT GTT ACT CGA GAG GCC AGT GCT GAG GAA GCA     GAT GTG CAC GTA GCT GTG GTG AGA CCA AAC GCA GGA TTA ACA GAT GAT     GAG AAG ACT TAC TAC AGC CTC ATC ACA TCC TTC AGT GAA CTA TAC CTG CCT TCC     TCA ACC TAG AGA AGG GTT GTT AAG GCA GAC CGC CCT GTT CCC CAG AGT TGT CCC     TGT AGT GTC TAG GTT TAT TCT AAT GGT AAA AGT AAC TTA CTT AAA CAT ATG     TAC ACA TAT GTA TGC AAG TAT GTA TAT ATG TGT ATG CTC AGA TTA ACT TCC ATA
 V   E   S   E   S   Y   R   K   I   A   D   S   I   G   C   S   T   N      N   I   L   F   L   T   D   V   T   R   E   A   S   A   E   E   A      D   V   H   V   A   V   V   R   P   N   A   G   L   T   D   D      E   K   T   Y   Y   S   L   I   T   S   F   S   E   L   Y   L   P   S
 S   T
```

FIGURE 2C

```
          1144      1153      1162      1171      1180      1189
GGT ACA TAA GTG AAA GAA GTC TCA GTT CAG TGA ACA CAA AAC TTA TTT AAA GAT 1198      1207      1216      1225      1234      1243
GCT TTA TAT GTA GAA ATT GTT TCA AAT CAT ACT CTA ACC CTT AGT GAG GGC AAA 1252      1261      1270      1279      1288      1297
GTG TAG TTG GTA GAA GAA ATT GCT AAA TAC CTA TCT AAT GTG CTA TGT TTA TCA 1306      1315      1324      1333      1342      1351
AAT CGT GTA CTA AAA TGG AAA GCT AGT TTT GAG AAA TTA TTC AGA AGC CTT GTT 1360      1369      1378      1387      1396      1405
ATT TTA AAA ATG AAA TAT TTC AAA GAC TGA ATA TTT TCA AAG AAA ATG AAT AAT 1414      1423      1432      1441      1450      1459
TCA TTG CCC TTG TGA TTT AGA AGA TTA TAA CAG CTG TAT TTC ATA TTT GCC TCC 1468      1477      1486      1495      1504      1513
TTA TAT ATA TCA AAG GTA ACC AAG GTA TTT CCT TCT GCT TCA AAA GAA CAA AAT TGG 1522      1531      1540      1549      1558      1567
GAA AGA AAA CTC ACT TGA GTC TTG ATC AAA CAA GTG TCT TTT ACT TAA GAA GAA
```

FIGURE 2D

```
     1576      1585      1594      1603      1612      1621
ACT TGG TAA TCA TTG TGG CAC CCA CAG CAA GCA GTT GCC TTA CCA GTG AAA AAG
     1630      1639      1648      1657      1666      1675
GTG CAC TGA GGT AAC ATC TAA AAC AGA GAT GTG GTT CTT AAT GTT TAA CAG AAC
     1684      1693      1702      1711      1720      1729
AGT TCT AAT CCT GCC ACG TGT TAT CAT TAT AGA TTT TAT AGT TGC CTT TCT AAC
     1738      1747      1756      1765      1774      1783
TAC TTA GCA CAG TTT GAG AAT ACG TTA ATT GCT ATT TAC TAT TTA AAA AGT TTT
     1792      1801      1810      1819      1828      1837
ACT GAA ATC AGT CCA TAA CAT TAA GAT GAG CCC TAA TAT GTA AGA TTT TCC TCT
     1846      1855      1864      1873      1882      1891
GGA ATG GAT GTG AGA AAT GTA AAT TTT ATA ACA GCA GTA TTT ATC CTG GTT TAA
     1900      1909      1918      1927      1936      1945
TTC TAA TAC GAT GTC ATG TTA ATT TCA TGT TGT GAT TAA TAA AAG CAT TTT TTC
     1954      1963
TTC ACT CAA AAA AAA AAC GGT CGA G 3'
```

FIGURE 2E

```
              11          20          29          38          47          56
5' GGACA  ATC ACC AGA GAG CTG AAT TTT ACA TTG ATT TCA CAT GTT TGT GTC TTA GGT 65          74          83          92          101         110
   GAC TTT TCC CAA CTG TTA ATT GAT AGA AAA TGA TTT GTC TGT ATC CTT GAA AGA 119         128         137         146         155         164
   TTG TAC TGT ATT ATT TAA AAA AAA ACC CTC TAA TCT TCC CAT TTG ACA AAT GTG 173         182         191         200         209         218
   ACA GAA GGC TGT GAT GAA TCA GTA GCA TTT AAA TCT TCC CAT ACC CTG ACA CTG ACA CAT ACC TGT ATT 227         236         245         254         263         272
   TTG CAG CGC GCG GCG CGG CCA GCC CGC AGA AGC CGG TGG CCG AGG AGG ACG 281         290         299         308         317         326
   GAG CCC TAA CCG CAA CCC GCG CGC CGC GCC CCG ATT TGA TTT GTA TCC 335         344         353         362         371         380
   ACT GTC ACC AGC ACT GCT CAC TTA GGA CTT TCT TCT GGA TCC AGA CCC AGG CGC 389         398         407         416         425         434
   ACA CTG GAC TCT TGA GGA AGA AGG AGA CTC TAA TTT TGG ATT CCT TGG TGG AGG
```

```
     443         452         461         470         479         488
AAA ATA AAA CAC TCT GGT CTT GCC AAC GAT GCA AGT GTG ACT GCT GGC GTC
 K   I   K   H   S   G   L   A   N   D   A   S   V   T   A   G   V 497         506         515         524         533         542
TTC ATG AGC TCC AGA GGT CAC AGC ACG CTA CCA AGG ACT CTC ATG GCC CCT CGG
 F   M   S   S   R   G   H   S   T   L   P   R   T   L   M   A   P   R 551         560         569         578         587         596
ATG ATT TCC GAG GGA GAC ATA GGA GGC ATT GCT CAA ATC ACC TCC TCT CTA TTC
 M   I   S   E   G   D   I   G   G   I   A   Q   I   T   S   S   L   F 605         614         623         632         641         650
CTG GGC AGA GGC AGT GTG GCC TCC AAT CGG CAC CTC CTC CAG GCT CGT GGC ATC
 L   G   R   G   S   V   A   S   N   R   H   L   L   Q   A   R   G   I 659         668         677         686         695         704
ACC TGC ATT GTT AAT GCT ACC ATT GAG ATC CCT AAT TTC AAC TGG CCC CAA TTT
 T   C   I   V   N   A   T   I   E   I   P   N   F   N   W   P   Q   F 713         722         731         740         749         758
GAG TAT GTT AAA GTG CCT CTG GCT ATG CCG CAT GCC CCC ATT GGA CTG TAC
 E   Y   V   K   V   P   L   A   M   P   H   A   P   I   G   L   Y 767         776         785         794         803         812
TTT GAC ACC GTG GCT GAC AAG ATC CAC AGT GTG AGC AGG AAG CAC GGG GCC ACC
 F   D   T   V   A   D   K   I   H   S   V   S   R   K   H   G   A   T
```

FIGURE 3C

```
     821             830             839             848             857             866
     TTG GTG CAC     TGT GCT GCA     GGG GTG AGC     CGC TCA GCC     ACG CTG TGT     ATC GCG TAC
      L   V   H       C   A   A       G   V   S       R   S   A       T   L   C       I   A   Y 875             884             893             902             911             920
     CTG ATG AAA     TTC CAC AAC     GTG TGC CTG     GAG CTG CTG     GAG GCG TAC     AAC TGG GTG AAA GCC
      L   M   K       F   H   N       V   C   L       E   L   L       E   A   Y       N   W   V   K   A 929             938             947             956             965             974
     CGG CGA CCT     GTC ATC AGG     CCC AAC GTA     GGC TTC TGG     AGG CAA CTG     ATA GAC TAC
      R   R   P       V   I   R       P   N   V       G   F   W       R   Q   L       I   D   Y 983             992             1001            1010            1019            1028
     GAG CGC CAG     CTC TTT GGG     AAG TCG ACA     GTT AAA ATG     GTA CAG ACA     CCT TAT GGC
      E   R   Q       L   F   G       K   S   T       V   K   M       V   Q   T       P   Y   G 1037            1046            1055            1064            1073            1082
     ATA GTT CCC     GAC GTC TAT     GAG AAG TCC     CGA CAC CTG     ATG GTA CCT     TAC TGG GGG
      I   V   P       D   V   Y       E   K   S       R   H   L       M   V   P       Y   W   G 1091            1100            1109            1118            1127            1136
     ATT TAG TGC     CAC TGA AGC     CTG CGT CAG     CAG CCC GAG     CGG GGC CGG     CAT CTG CTC
      I 1145            1154            1163            1172            1181            1190
     CCC GCC GTC     TGC TCC CTC     TCC ACT CTC     TTC TCA AAT     GGC TGA CTT     CTG GTT CTC
```

```
                    1199          1208          1217          1226          1235          1244
               CCT CAA GTG TTT TTT ACA CTG GGT GTT CAA ATT TAT TTT AAG AGA TAG GGA GGG 1253          1262          1271          1280          1289          1298
               AGG GGA CAT AAA GGG AAT GCA TAC ATT GCT AGT CAC ATT TTT AAA ATT AAC ATT 1307          1316          1325          1334          1343          1352
               TTG GAA TAG TGT TTA TGG AAA TCT TTA GCT TTT AAT CAT TTT TAC CAA TTT GAA 1361          1370          1379          1388          1397          1406
               CAG TTT AAT AAA CTG GTT CTG CTC TCT TCT GAA TCT CAT GCC TTT GGC ACC TTG 1415          1424          1433          1442          1451          1460
               GTA GGT GCA GGA GCT CAG TGC AAA AAT CAC TTT GGG GCC TCA TTA ACC CTT 1469          1478          1487          1496          1505          1514
               TAG AGA CAA GCT TTG CCC CAG GCT GCG GAC CAG ACA GAT GCT TAG GGA AGG TTG 1523          1532          1541          1550          1559          1568
               ATA ACC AGC TTC AGT CTC TAC TGG ATT AGC CCT ACT CTT TCC TTT CCC CTC CAT 1577          1586          1595          1604          1613          1622
               TAT TTA GTG ACT CTG TAA GTA AGT TAA ATA CAC CCT TAT TAT TTA GCT GTT AAG
```

FIGURE 3D

```
     1631           1640           1649          1658           1667           1676
TAA CTA TAA TGA AAT CTG CTG CAA AAT CTC TCT TGG AAT CCA TGT GCC CAG GAT 1685           1694           1703          1712           1721
TAT ATT AGC ATT ATT TTT AAT AAA TCT ATA TGC TTA ACA TAT TAA AAA AAA AA 3'
```

FIGURE 3E

|     |                                                          |          |
| --- | -------------------------------------------------------- | -------- |
| 1   | M V V L S V P A E V T V I L L D I E G T T T P I A F V K D I | 2534680  |
| 1   | M I - - - - - R A I V T D I E G T T S D I R F V H N V   | GI401712 |
| 31  | L F P Y I E E N V K E Y L Q T H W E E E C Q Q D V S L L R | 2534680  |
| 23  | L F P Y A R E R L A G F V T A - - - - - Q Q F V E P V K | GI401712 |
| 61  | K Q A E E D A H L D G A V P I P A A S G N G V D D L Q Q M I | 2534680  |
| 46  | T I L D - - N L R E E I A Q P A A - - G A E E L I A T L | GI401712 |
| 91  | Q A V V D N V C W Q M S L D R K T T A L K Q L Q G H M W R A | 2534680  |
| 70  | F A F M D E - - - - - D R K S T A L K A L Q G I I W R D | GI401712 |
| 121 | A F T A G R M K A E F F A D V V P A V R K W R E A G M K V Y | 2534680  |
| 93  | G Y V H G D F T G H L Y P D V L P A L E K W K S Q G I D L Y | GI401712 |
| 151 | I Y S S G S V E A Q K L L F G H S T E G D I L E L V D G H F | 2534680  |
| 123 | V Y S S G S V A A Q K L L F G Y S D E G D I T H L F N G Y F | GI401712 |

FIGURE 4A

```
181  DTKIGHKVESESYRKIADSIGCSTNNILFL      2534680
153  DTLVGAKREAQSYRNIAEQLGQPPAAILFL      GI401712

211  TDVTREASAAEEADVHVAVVVRPGNAGLTD      2534680
183  SDIHQELDAAEEAGFRTLQLVRGDR----      GI401712

241  DEKTYYSLITSFSELYL-PSST              2534680
208  DPASHHPQVQRFDDIHPEQIPA              GI401712
```

FIGURE 4B

```
1   MSSRGHSTLPRTLMAPRMISEGDIGGIAQI  3041794
1   MT-----------LSFRVNPE--YAAMSEI  GI1495338

31  TSSLFLGRGSVASNRHLLQARGITCIVNAT  3041794
18  VPGLFIC-GVSALSKDEMKKHKITHIINAT  GI1495338

61  IEIPNF-NWPQFEYVKVPLADMPHAPIGLY  3041794
47  TEVPNLRSLGDIQRTKLWLEDTPQTYIYPH  GI1495338

90  FDTVADKIHSVRKHGATLVHCAAGVSRSA   3041794
77  LELQSDQHQALIADGGKVLVHCVAGVSRSA  GI1495338
```

PROTEIN PHOSPHATASE-RELATED MOLECULES

FIELD OF THE INVENTION

This invention relates to nucleic acid and amino acid sequences of protein phosphatase-related molecules and to the use of these sequences in the diagnosis, treatment, and prevention of cancer and immune and reproductive disorders.

BACKGROUND OF THE INVENTION

Phosphatases remove phosphate groups from molecules previously activated by kinases and control most cellular signaling events that regulate cell growth and differentiation, cell-to-cell contacts, the cell cycle and oncogenesis. Protein phosphorylation is the ubiquitous strategy used to control the activities of eukaryotic cells. It is estimated that more than 1000 of the 10,000 proteins active in a typical mammalian cell are phosphorylated. In phosphorylation, the high energy phosphate which confers activation is transferred from adenosine triphosphate molecules to a protein by protein kinases, and is subsequently removed from the protein by protein phosphatases.

There appear to be three evolutionarily-distinct protein phosphatase gene families: protein phosphatases (PPs); protein tyrosine phosphatases (PTPs); and acid/alkaline phosphatases (APs). PPs dephosphorylate phosphoserine/threonine residues and are an important regulator of many cAMP-mediated hormone responses in cells. PTPs reverse the effects of protein tyrosine kinases and play a significant role in cell cycle and cell signaling processes. APs dephosphorylate substrates in vitro, although their role in vivo is not well known.

PPs may be cytosolic or associated with a receptor and can be separated into four distinct groups: PP-I, PP-IIA, PP-IIB, and PP-TIC. (Cohen, P. (1989) Annu. Rev. Biochem. 58:453–508.) PP-IIC is a relatively minor phosphatase that is unrelated to the other three. The three principle PPs are composed of a homologous catalytic subunit coupled with one or more regulatory subunits. PP-I dephosphorylates many of the proteins phosphorylated by cylic AMP-dependent protein kinase (PKA) and is an important regulator of many cyclic AMP-mediated hormone responses in cells. PP-IIA has broad specificity for control of cell cycle, growth, and proliferation, and DNA replication, and is the main phosphatase responsible for reversing the phosphorylations of serine/threonine kinases. PP-IIB, or calcineurin (Cn), is a $Ca^{+2}$ activated phosphatase and is particularly abundant in the brain.

PTPs remove phosphate groups from selected phosphotyrosines on particular types of proteins. In so doing, PTPs reverse the effects of protein tyrosine kinases (PTK) and play a significant role in cell cycle and cell signaling processes. (Charbonneau, H. and Tonks, N. K. (1992) Annu. Rev. Cell Biol. 8:463–493.) PTPs possess a high specific enzyme activity relative to their PTK counterparts. In the process of cell division, for example, a specific PTP (M-phase inducer phosphatase) plays a key role in the induction of mitosis by dephosphorylating and activating a specific PTK (CDC2) leading to cell division. (Krishna, S. et al. (1990) Proc. Natl. Acad. Sci. 87:5139–5143.) Tyrosine phosphorylations are therefore short lived and uncommon in resting cells.

Many PTKs are encoded by oncogenes, and it is well known that oncogenesis is often accompanied by increased tyrosine phosphorylation activity. It is therefore possible that PTPs may serve to prevent or reverse cell transformation and the growth of various cancers by controlling the levels of tyrosine phosphorylation in cells. This is supported by studies showing that overexpression of PTP can suppress transformation in cells and that specific inhibition of PTP can enhance cell transformation. (Charbonneau and Tonks, supra.)

PTPs are found in transmembrane, receptor-like and nontransmembrane, non-receptor forms, and are diverse in size (from 20 kDa to greater than 100 kDa) and structure. All PTPs share homology within a region of 240 residues which delineates the catalytic domain and contains the common sequence VHCXAGXXR near the carboxy terminus. The combination of the catalytic domain with a wide variety of structural motifs accounts for the diversity and specificity of these enzymes. In nonreceptor isoforms, noncatalytic sequences may also confer different modes of regulation and target PTPs to various intracellular compartments.

The discovery of new protein phosphatase-related molecules and the polynucleotides encoding them satisfies a need in the art by providing new compositions which are useful in the diagnosis, treatment, and prevention of cancer and immune and reproductive disorders.

SUMMARY OF THE INVENTION

The invention features substantially purified polypeptides, protein phosphatase-related molecules, referred to collectively as "PPRM" and individually as "PPRM-1", "PPRM-2", and "PPRM-3." In one aspect, the invention provides a substantially purified polypeptide comprising an amino acid sequence selected from the group consisting of SEQ ID NO: 1, SEQ ID NO:3, SEQ ID NO:5, a fragment of SEQ ID NO:1, a fragment of SEQ ID NO:3, and a fragment of SEQ ID NO:5.

The invention further provides a substantially purified variant having at least 90% amino acid identity to the amino acid sequences of SEQ ID NO: 1, SEQ ID NO:3, SEQ ID NO:5 or to a fragment of any of these sequences. The invention also provides an isolated and purified polynucleotide encoding the polypeptide comprising an amino acid sequence selected from the group consisting of SEQ ID NO: 1, SEQ ID NO:3, SEQ ID NO:5, a fragment of SEQ ID NO: 1, a fragment of SEQ ID NO:3, and a fragment of SEQ ID NO:5. The invention also includes an isolated and purified polynucleotide variant having at least 90% polynucleotide sequence identity to the polynucleotide encoding the polypeptide comprising an amino acid sequence selected from the group consisting of SEQ ID NO: 1, SEQ ID NO:3, SEQ ID NO:5, a fragment of SEQ ID NO: 1, a fragment of SEQ ID NO:3, and a fragment of SEQ ID NO:5.

Additionally, the invention provides an isolated and purified polynucleotide which hybridizes under stringent conditions to the polynucleotide encoding the polypeptide comprising an amino acid sequence selected from the group consisting of SEQ ID NO: 1, SEQ ID NO:3, SEQ ID NO:5, a fragment of SEQ ID NO:1, a fragment of SEQ ID NO:3, and a fragment of SEQ ID NO:5, as well as an isolated and purified polynucleotide having a sequence which is complementary to the polynucleotide encoding the polypeptide comprising the amino acid sequence selected from the group consisting of SEQ ID NO:1, SEQ ID NO:3, SEQ ID NO:5, a fragment of SEQ ID NO:1, a fragment of SEQ ID NO:3, and a fragment of SEQ ID NO:5.

The invention also provides an isolated and purified polynucleotide comprising a polynucleotide sequence selected from the group consisting of SEQ ID NO:2, SEQ ID NO:4, SEQ ID NO:6, a fragment of SEQ ID NO:2, a fragment of SEQ ID NO:4, and a fragment of SEQ ID NO:6. The invention further provides an isolated and purified polynucleotide variant having at least 90% polynucleotide sequence identity to the polynucleotide sequence comprising a polynucleotide sequence selected from the group consisting of SEQ ID NO:2, SEQ ID NO:4, SEQ ID NO:6, a fragment of SEQ ID NO:2, a fragment of SEQ ID NO:4, and a fragment of SEQ ID NO:6, as well as an isolated and purified polynucleotide having a sequence which is complementary to the polynucleotide comprising a polynucleotide sequence selected from the group consisting of SEQ ID NO:2, SEQ ID NO:4, SEQ ID NO:6, a fragment of SEQ ID NO:2, a fragment of SEQ ID NO:4, and a fragment of SEQ ID NO:6.

The invention further provides an expression vector containing at least a fragment of the polynucleotide encoding the polypeptide comprising an amino acid sequence selected from the group consisting of SEQ ID NO: 1, SEQ ID NO:3, SEQ ID NO:5, a fragment of SEQ ID NO: 1, a fragment of SEQ ID NO:3, and a fragment of SEQ ID NO:5. In another aspect, the expression vector is contained within a host cell.

The invention also provides a method for producing a polypeptide comprising the amino acid sequence selected from the group consisting of SEQ ID NO: 1, SEQ ID NO:3, SEQ ID NO:5, a fragment of SEQ ID NO: 1, a fragment of SEQ ID NO:3, and a fragment of SEQ ID NO:5, the method comprising the steps of: (a) culturing the host cell containing an expression vector containing at least a fragment of a polynucleotide encoding the polypeptide under conditions suitable for the expression of the polypeptide; and (b) recovering the polypeptide from the host cell culture.

The invention also provides a pharmaceutical composition comprising a substantially purified polypeptide having the amino acid sequence selected from the group consisting of SEQ ID NO: 1, SEQ ID NO:3, SEQ ID NO:5, a fragment of SEQ ID NO: 1, a fragment of SEQ ID NO:3, and a fragment of SEQ ID NO:5 in conjunction with a suitable pharmaceutical carrier.

The invention further includes a purified antibody which binds to a polypeptide comprising the amino acid sequence selected from the group consisting of SEQ ID NO:1, SEQ ID NO:3, SEQ ID NO:5, a fragment of SEQ ID NO: 1, a fragment of SEQ ID NO:3, and a fragment of SEQ ID NO:5, as well as a purified agonist and a purified antagonist to the polypeptide.

The invention also provides a method for treating or preventing a cancer, the method comprising administering to a subject in need of such treatment an effective amount of a pharmaceutical composition comprising a substantially purified polypeptide having an amino acid sequence selected from the group consisting of SEQ ID NO: 1, SEQ ID NO:3, SEQ ID NO:5, a fragment of SEQ ID NO: 1, a fragment of SEQ ID NO:3, and a fragment of SEQ ID NO:5.

The invention also provides a method for treating or preventing an immune disorder, the method comprising administering to a subject in need of such treatment an effective amount of a pharmaceutical composition comprising a substantially purified polypeptide having an amino acid sequence selected from the group consisting of SEQ ID NO: 1, SEQ ID NO:3, SEQ ID NO:5, a fragment of SEQ ID NO: 1, a fragment of SEQ ID NO:3, and a fragment of SEQ ID NO:5.

The invention also provides a method for treating or preventing a reproductive disorder, the method comprising administering to a subject in need of such treatment an effective amount of a pharmaceutical composition comprising a substantially purified polypeptide having an amino acid sequence selected from the group consisting of SEQ ID NO:1, SEQ ID NO:3, SEQ ID NO:5, a fragment of SEQ ID NO: 1, a fragment of SEQ ID NO:3, and a fragment of SEQ ID NO:5.

The invention also provides a method for detecting a polynucleotide encoding the polypeptide comprising the amino acid sequence selected from the group consisting of SEQ ID NO: 1, SEQ ID NO:3, SEQ ID NO:5, a fragment of SEQ ID NO: 1, a fragment of SEQ ID NO:3, and a fragment of SEQ ID NO:5 in a biological sample containing nucleic acids, the method comprising the steps of: (a) hybridizing the complement of the polynucleotide sequence encoding the polypeptide comprising the amino acid sequence selected from the group consisting of SEQ ID NO: 1, SEQ ID NO:3, SEQ ID NO:5, a fragment of SEQ ID NO: 1, a fragment of SEQ ID NO:3, and a fragment of SEQ ID NO:5 to at least one of the nucleic acids of the biological sample, thereby forming a hybridization complex; and (b) detecting the hybridization complex, wherein the presence of the hybridization complex correlates with the presence of a polynucleotide encoding the polypeptide in the biological sample. In one aspect, the nucleic acids of the biological sample are amplified by the polymerase chain reaction prior to the hybridizing step.

BRIEF DESCRIPTION OF THE FIGURES

FIGS. 1A, 1B, 1C, and 1D show the amino acid sequence (SEQ ID NO:1) and nucleic acid sequence (SEQ ID NO:2) of PPRM-1. The alignment was produced using MacDNASIS PRO™ software (Hitachi Software Engineering Co. Ltd., San Bruno, Calif.).

FIGS. 2A, 2B, 2C, 2D, and 2E show the amino acid sequence (SEQ ID NO:3) and nucleic acid sequence (SEQ ID NO:4) of PPRM-2. The alignment was produced using MacDNASIS PRO™ software.

FIGS. 3A, 3B, 3C, 3D, and 3E show the amino acid sequence (SEQ ID NO:5) and nucleic acid sequence (SEQ ID NO:6) of PPRM-3. The alignment was produced using MacDNASIS PRO™ software.

FIGS. 4A and 4B show the amino acid sequence alignments between PPRM-2 (2534680; SEQ ID NO:3) and an enolase-phosphatase from *Klebsiella oxytoca*, E-1 (GI 401712; SEQ ID NO:7), produced using the multisequence alignment program of LASERGENE™ software (DNASTAR Inc, Madison Wis.).

FIGS. 5A and 5B show the amino acid sequence alignments between PPRM-3 (3041794; SEQ ID NO:5) and a protein-tyrosine phosphatase-related molecule from *Caenorhabditis elegans* (GI 1495338; SEQ ID NO:8), produced using the multisequence alignment program of LASERGENE™ software.

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

Definitions

"PPRM," as used herein, refers to the amino acid sequences of substantially purified PPRM obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to PPRM, increases or prolongs the duration of the effect of PPRM. Agonists may include proteins, nucleic acids, carbohydrates, or any other molecules which bind to and modulate the effect of PPRM.

An "allele" or an "allelic sequence," as these terms are used herein, is an alternative form of the gene encoding PPRM. Alleles may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding PPRM, as described herein, include those sequences with deletions, insertions, or substitutions of different nucleotides, resulting in a polynucleotide the same PPRM or a polypeptide with at least one functional characteristic of PPRM. Included within this definition are polymorphisms which may or may not be readily detectable using a particular oligonucleotide probe of the polynucleotide encoding PPRM, and improper or unexpected hybridization to alleles, with a locus other than the normal chromosomal locus for the polynucleotide sequence encoding PPRM. The encoded protein may also be "altered," and may contain deletions, insertions, or substitutions of amino acid residues which produce a silent change and result in a functionally equivalent PPRM. Deliberate amino acid substitutions may be made on the basis of similarity in polarity, charge, solubility, hydrophobicity, hydrophilicity, and/or the amphipathic nature of the residues, as long as the biological or immunological activity of PPRM is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments", "immunogenic fragments", or "antigenic fragments" refer to fragments of PPRM which are preferably about 5 to about 15 amino acids in length and which retain some biological activity or immunological activity of PPRM. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual*, Cold Spring Harbor Press, Plainview, N.Y., pp. 1–5.)

The term "antagonist," as it is used herein, refers to a molecule which, when bound to PPRM, decreases the amount or the duration of the effect of the biological or immunological activity of PPRM. Antagonists may include proteins, nucleic acids, carbohydrates, antibodies, or any other molecules which decrease the effect of PPRM.

As used herein, the term "antibody" refers to intact molecules as well as to fragments thereof, such as Fa, $F(ab')_2$, and Fv fragments, which are capable of binding the epitopic determinant. Antibodies that bind PPRM polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to a specific nucleic acid sequence. The term "antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic PPRM, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation, an aqueous solution, or a sterile composition. Compositions comprising polynucleotide sequences encoding PPRM or fragments of PPRM may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS), and other components (e.g., Denhardt's solution, dry milk, salmon sperm DNA, etc.).

"Consensus sequence," as used herein, refers to a nucleic acid sequence which has been resequenced to resolve uncalled bases, extended using XL-PCRTM (Perkin Elmer, Norwalk, Conn.) in the 5' and/or the 3' direction, and resequenced, or which has been assembled from the overlapping sequences of more than one Incyte Clone using a computer program for fragment assembly, such as the GELVIEW™ Fragment Assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding PPRM, by northern analysis is indicative of the presence of nucleic acids encoding PPRM in a sample, and thereby correlates with expression of the transcript from the polynucleotide encoding PPRM.

A "deletion," as the term is used herein, refers to a change in the amino acid or nucleotide sequence that results in the absence of one or more amino acid residues or nucleotides.

The term "derivative," as used herein, refers to the chemical modification of PPRM, of a polynucleotide sequence encoding PPRM, or of a polynucleotide sequence complementary to a polynucleotide sequence encoding PPRM. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "homology," as used herein, refers to a degree of complementarity. There may be partial homology or complete homology. The word "identity" may substitute for the word "homology." A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay (Southern or northern blot, solution hybridization, and the like) under conditions of reduced stringency. A substantially homologous sequence or hybridization probe will compete for and inhibit the binding of a completely homologous sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% homology or identity). In the absence of non-specific binding, the substantially homologous sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MegAlign™ program (DNASTAR, Inc., Madison Wis.). The MegAlign™ program can create alignments between two or more sequences according to different methods, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" as used herein, refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray," as used herein, refers to an arrangement of distinct polynucleotides arrayed on a substrate, e.g., paper, nylon or any other type of membrane, filter, chip, glass slide, or any other suitable solid support.

The terms "element" or "array element" as used herein in a microarray context, refer to hybridizable polynucleotides arranged on the surface of a substrate.

The term "modulate," as it appears herein, refers to a change in the activity of PPRM. For example, modulation may cause an increase or a decrease in protein activity, binding characteristics, or any other biological, functional, or immunological properties of PPRM.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which are greater than about 60 nucleotides in length, and most preferably are at least about 100 nucleotides, at least about 1000 nucleotides, or at least about 10,000 nucleotides in length.

The terms "operably associated" or "operably linked," as used herein, refer to functionally related nucleic acid sequences. A promoter is operably associated or operably linked with a coding sequence if the promoter controls the transcription of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimer," "primer," "oligomer," and "probe," as these terms are commonly defined in the art.

"Peptide nucleic acid" (PNA), as used herein, refers to an antisense molecule or to anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA and RNA and stop transcript elongation, and may be pegylated to extend their lifespan in the cell. (See, e.g., Nielsen, P. E. et al. (1993) Anticancer Drug Des. 8:53–63.)

The term "sample," as used herein, is used in its broadest sense. A biological sample suspected of containing nucleic acids encoding PPRM, or fragments thereof, or PPRM itself, may comprise a bodily fluid; an extract from a cell, chromosome, organelle, or membrane isolated from a cell; a cell; genomic DNA, RNA, or cDNA, in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotide sequences and the claimed polynucleotide sequences. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5× SSPE, 0.3% SDS, and 200 μg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of PPRM, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE™ software.

THE INVENTION

The invention is based on the discovery of new human protein phosphatase-related molecules (PPRM), the polynucleotides encoding PPRM, and the use of these compositions for the diagnosis, treatment, or prevention of cancer and immune and reproductive disorders.

Nucleic acids encoding PPRM-1 of the present invention were first identified in Incyte Clone 1359553 from the lung cDNA library (LUNGNOT12) using a computer search for amino acid sequence alignments. A consensus sequence, SEQ ID NO:2, was derived from the following overlapping and/or extended nucleic acid sequences: Incyte Clones 1359553 (LUNGNOT12), 1315677 (BLADTUT02), 1533139 (SPLNNOT04), and 1541615 (SINTTUT01).

In one embodiment, the invention encompasses a polypeptide comprising the amino acid sequence of SEQ ID NO:1, as shown in FIGS. 1A, 1B, 1C, and 1D. PPRM-1 is 303 amino acids in length and has potential phosphorylation sites for casein kinase II at residues S25, S109, S149, and S216, for protein kinase C at T64 and S93, and for tyrosine kinase at Y230. PPRM-1 has a sequence related to the mitotic, M-phase inducer phosphatase signature sequence between residues L80 and L100, and a phosphotyrosine phosphatase-related signature sequence between residues M286 and G298. PPRM-1 has chemical and structural homology with a mouse phosphoprotein phosphatase (GI 567040; SEQ ID NO:9). In particular, PPRM-1 and the mouse PP share 26% identity. The fragment of SEQ ID NO:2 from about nucleotide 364 to about nucleotide 434 is useful for hybridization. Northern analysis shows the expression of this sequence in various, libraries, at least 51 % of which are immortalized or cancerous, at least 35% of which involve inflammation and the immune response, and at least 29% of which involve reproductive tissues. Of particular note is expression of PPRM-1 associated with cancers of brain, bladder, prostate, liver, uterus, testicles, penis, ovaries, breast and colon, and with inflammatory disorders including rheumatoid and osteoarthritis, ulcerative colitis, asthma, biliary cirrhosis, Crohn's disease, and lymphocytic thyroiditis.

Nucleic acids encoding PPRM-2 of the present invention were first identified in Incyte Clone 2534680 from the brain cDNA library (BRAINOT18) using a computer search for amino acid sequence alignments. A consensus sequence, SEQ ID NO:4, was derived from the following overlapping and/or extended nucleic acid sequences: Incyte Clones 486995 (HNT2AGT01), 1811013 (PROSTUT12), 1685831 (PROSNOT15), 1493171 (PROSNON01), 1864060 (PROSNOT19), 1872023 (LEUKNOT02), and 2534680 (BRAINOT18).

In another embodiment, the invention encompasses a polypeptide comprising the amino acid sequence of SEQ ID NO:3, as shown in FIGS. 2A, 2B, 2C, 2D, and 2E. PPRM-2 is 261 amino acids in length and has potential phosphorylation sites for cAMP and cGMP-dependent protein kinase at T108, for casein kinase II at T45, T168, S218, T239, and S251, and for protein kinase C at S 192. As shown in FIGS. 4A and 4B, PPRM-2 shares chemical and structural homology with an enolase-phosphatase from K. oxytoca E-1 (GI 401712; SEQ ID NO:7). In particular, PPRM-2 and the E-1 enzyme share 36% identity and the two potential phosphorylation sites found in PPRM-2 at T108 and S192. The fragment of SEQ ID NO:4 from about nucleotide 365 to about nucleotide 419 is useful for hybridization. Northern analysis shows the expression of this sequence in various libraries, at least 58% of which are immortalized or cancerous, at least 23% of which involve inflammation and the immune response, and at least 33% of which involve reproductive tissues. Of particular note is expression of PPRM-2 associated with cancers of the brain, thyroid, testicles, penis, ovaries, lung, colon, breast, and bladder.

Nucleic acids encoding PPRM-3 of the present invention were first identified in Incyte Clone 3041794 from the breast cDNA library (BRSTNOT16) using a computer search for amino acid sequence alignments. A consensus sequence, SEQ ID NO:6, was derived from the following overlapping and/or extended nucleic acid sequences: Incyte Clones 3041794 (BRSTNOT16), 1395671 (THYRNOT03), 1433617 (BEPINONO01), and 070030 (HUVESTB01).

In another embodiment, the invention encompasses a polypeptide comprising the amino acid sequence of SEQ ID NO:5, as shown in FIGS. 3A, 3B, 3C, 3D, and 3E. PPRM-3 is 198 amino acids in length and has a potential signal peptide sequence from M14 to S43, a potential N-glycosylation site at N58, and potential phosphorylation sites for casein kinase II at S20 and T92, and for protein kinase Cat S2, S43,S101, and T170. PPRM-3 also contains a tyrosine-specific, protein phosphatase active site sequence between residues V109 and L121, in which C111 is the active site cysteine residue. As shown in FIGS. 5A and 5B, PPRM-3 shares chemical and structural homology with a protein-tyrosine phosphatase-related molecule from C. elegans (GI 1495338; SEQ ID NO:8) In particular, PPRM-3 and the C. elegans PTP share 27% identity. The two proteins share the N-glycosylation site and the potential phosphorylation site at T170 in PPRM-3, and the PTP active site sequence is highly conserved between the two proteins, including the active site cysteine. The fragment of SEQ ID NO:6 from about nucleotide 750 to about nucleotide 814 is useful for hybridization. Northern analysis shows the expression of this sequence in various libraries, at least 5 1 % of which are immortalized or cancerous, at least 32% of which involve inflammation and the immune response, and at least 23% of which involve reproductive tissues. Of particular note is expression of PPRM-3 associated with cancers of the brain, thyroid, stomach, lung, and bladder, and with inflammatory disorders including ulcerative colitis, osteoarthritis, and Crohn's disease.

The invention also encompasses PPRM variants. A preferred PPRM variant is one which has at least about 80%, more preferably at least about 90%, and most preferably at least about 95% amino acid sequence identity to the PPRM amino acid sequence, and which contains at least one functional or structural characteristic of PPRM.

The invention also encompasses polynucleotides which encode PPRM. In a particular embodiment, the invention encompasses a polynucleotide sequence comprising the sequence of SEQ ID NO:2, which encodes a PPRM. In a further embodiment, the invention encompasses the polynucleotide sequence comprising the sequence of SEQ ID NO:4, as shown in FIGS. 2A, 2B, 2C, 2D, and 2E. In still another embodiment, the invention encompasses the polynucleotide sequence comprising the sequence of SEQ ID NO:6, as shown in FIGS. 3A, 3B, 3C, 3D, and 3E.

The invention also encompasses a variant of a polynucleotide sequence encoding PPRM. In particular, such a variant polynucleotide sequence will have at least about 80%, more preferably at least about 90%, and most preferably at least about 95% polynucleotide sequence identity to the polynucleotide sequence encoding PPRM. In a particular aspect, the invention encompasses a variant of SEQ ID NO:2 which has at least about 80%, more preferably at least about 90%, and most preferably at least about 95% polynucleotide sequence identity to SEQ ID NO:2. The invention also encompasses a polynucleotide variant of SEQ ID NO:4 having at least about 80%, more preferably at least about 90%, and most preferably at least about 95% polynucleotide sequence identity to SEQ ID NO:4. The invention further encompasses a polynucleotide variant of SEQ ID NO:6 having at least about 80%, more preferably at least about 90%, and most preferably at least about 95% polynucleotide sequence identity to SEQ ID NO:6. Any one of the polynucleotide variants described above can encode an amino acid sequence which contains at least one functional or structural characteristic of PPRM.

It will be appreciated by those skilled in the art that as a result of the degeneracy of the genetic code, a multitude of polynucleotide sequences encoding PPRM, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring PPRM, and all such variations are to be considered as being specifically disclosed.

Although nucleotide sequences which encode PPRM and its variants are preferably capable of hybridizing to the nucleotide sequence of the naturally occurring PPRM under appropriately selected conditions of stringency, it may be advantageous to produce nucleotide sequences encoding PPRM or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding PPRM and its derivatives without altering the encoded amino acid sequences include the production of RNA transcripts having more desirable properties, such as a greater half-life, than transcripts produced from the naturally occurring sequence.

The invention also encompasses production of DNA sequences which encode PPRM and PPRM derivatives, or fragments thereof, entirely by synthetic chemistry. After production, the synthetic sequence may be inserted into any of the many available expression vectors and cell systems using reagents that are well known in the art. Moreover, synthetic chemistry may be used to introduce mutations into a sequence encoding PPRM or any fragment thereof.

Also encompassed by the invention are polynucleotide sequences that are capable of hybridizing to the claimed polynucleotide sequences, and, in particular, to those shown in SEQ ID NO:2, SEQ ID NO:4, SEQ ID NO:6, a fragment of SEQ ID NO:2, a fragment of SEQ ID NO:4, or a fragment of SEQ ID NO:6 under various conditions of stringency. (See, e.g., Wahl, G. M. and S. L. Berger (1987) Methods Enzymol. 152:399–407; Kimmel, A. R. (1987) Methods Enzymol. 152:507–511.)

Methods for DNA sequencing are well known and generally available in the art and may be used to practice any of the embodiments of the invention. The methods may employ such enzymes as the Klenow fragment of DNA polymerase I, Sequenase® (US Biochemical Corp., Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System (GIBCO/BRL, Gaithersburg, Md.). Preferably, the process is automated with machines such as the Hamilton Micro Lab 2200 (Hamilton, Reno, Nev,), Peltier Thermal Cycler (PTC200; MJ Research, Watertown, Mass.) and the ABI Catalyst and 373 and 377 DNA Sequencers (Perkin Elmer).

The nucleic acid sequences encoding PPRM may be extended utilizing a partial nucleotide sequence and employing various methods known in the art to detect upstream sequences, such as promoters and regulatory elements. For example, one method which may be employed, restriction-site PCR, uses universal primers to retrieve unknown sequence adjacent to a known locus. (See, e.g., Sarkar, G. (1993) PCR Methods Applic. 2:318–322.) In particular, genomic DNA is first amplified in the presence of a primer which is complementary to a linker sequence within the vector and a primer specific to a region of the nucleotide sequenc. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region. (See, e.g., Triglia, T. et al. (1988) Nucleic Acids Res. 16:8186.) The primers may be designed using commercially available software such as OLIGO 4.06 Primer Analysis software (National Biosciences Inc., Plymouth, Minn.) or another appropriate program to be about 22 to 30 nucleotides in length, to have a GC content of about 50% or more, and to anneal to the target sequence at temperatures of about 68° C. to 72° C. The method uses several restriction enzymes to generate a suitable fragment in the known region of a gene. The fragment is then circularized by intramolecular ligation and used as a PCR template.

Another method which may be used is capture PCR, which involves PCR amplification of DNA fragments adjacent to a known sequence in human and yeast artificial chromosome DNA. (See, e.g., Lagerstrom, M. et al. (1991) PCR Methods Applic. 1:111–119.) In this method, multiple restriction enzyme digestions and ligations may be used to place an engineered double-stranded sequence into an unknown fragment of the DNA molecule before performing PCR. Other methods which may be used to retrieve unknown sequences are known in the art. (See, e.g., Parker, J. D. et al. (1991) Nucleic Acids Res. 19:3055–3060.) Additionally, one may use PCR, nested primers, and PromoterFinder™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable in that they will include more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and a charge coupled device camera for detection of the emitted wavelengths. Output/light intensity may be converted to electrical signal using appropriate software (e.g., Genotyper™ and Sequence Navigator™, Perkin Elmer), and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode PPRM may be used in recombinant DNA molecules to direct expression of PPRM, or fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express PPRM.

As will be understood by those of skill in the art, it may be advantageous to produce PPRM-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter PPRM-encoding sequences for a variety of reasons including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding PPRM may be ligated to a heterologous sequence to encode a fusion protein. For example, to screen peptide libraries for inhibitors of PPRM activity, it may be useful to encode a chimeric PPRM protein that can be recognized by a commercially available antibody. A fusion protein may also be engineered to contain a cleavage site located between the PPRM encoding sequence and the heterologous protein sequence, so that PPRM may be cleaved and purified away from the heterologous moiety.

In another embodiment, sequences encoding PPRM may be synthesized, in whole or in part, using chemical methods well known in the art. (See, e.g., Caruthers, M. H. et al. (1980) Nucl. Acids Res. Symp. Ser. 215–223, and Horn, T. et al. (1980) Nucl. Acids Res. Symp. Ser. 225–232.)

Alternatively, the protein itself may be produced using chemical methods to synthesize the amino acid sequence of PPRM, or a fragment thereof. For example, peptide synthesis can be performed using various solid-phase techniques. (See, e.g., Roberge, J. Y. et al. (1995) Science 269:202–204.) Automated synthesis may be achieved using the ABI 431 A Peptide Synthesizer (Perkin Elmer). Additionally, the amino acid sequence of PPRM, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1984) *Proteins, Structures and Molecular Properties*, WH Freeman and Co., New York, N.Y.)

In order to express a biologically active PPRM, the nucleotide sequences encoding PPRM or derivatives thereof may be inserted into appropriate expression vector, i.e., a vector which contains the necessary elements for the transcription and translation of the inserted coding sequence.

Methods which are well known to those skilled in the art may be used to construct expression vectors containing sequences encoding PPRM and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview, N.Y., ch. 4, 8, and 16–17; and Ausubel, F. M. et al. (1995, and periodic supplements) *Current Protocols in Molecular Biology*, John Wiley & Sons, New York, N.Y., ch. 9, 13, and 16.)

A variety of expression vector/host systems may be utilized to contain and express sequences encoding PPRM. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

The "control elements" or "regulatory sequences" are those non-translated regions, e.g., enhancers, promoters, and 5' and 3' untranslated regions, of the vector and polynucleotide sequences encoding PPRM which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters, e.g., hybrid lacZ promoter of the Bluescript® phagemid (Stratagene, La Jolla, Calif) or pSport1™ plasmid (GIBCO/BRL), may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding PPRM, vectors based on SV40 or EBV may be used with an appropriate selectable marker.

In bacterial systems, a number of expression vectors may be selected depending upon the use intended for PPRM. For example, when large quantities of PPRM are needed for the induction of antibodies, vectors which direct high level expression of fusion proteins that are readily purified may be used. Such vectors include, but are not limited to, multifunctional *E. coli* cloning and expression vectors such as Bluescript® (Stratagene), in which the sequence encoding PPRM may be ligated into the vector in frame with sequences for the amino-terminal Met and the subsequent 7 residues of 13-galactosidase so that a hybrid protein is produced, and pIN vectors. (See, e.g., Van Heeke, G. and S. M. Schuster (1989) J. Biol. Chem. 264:5503–5509.) pGEX vectors (Amersham Pharmacia Biotech, Uppsala, Sweden) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae*, a number of vectors containing constitutive or inducible promoters, such as alpha factor, alcohol oxidase, and PGH, may be used. (See, e.g., Ausubel, supra; and Grant et al. (1987) Methods Enzymol. 153:516–544.)

In cases where plant expression vectors are used, the expression of sequences encoding PPRM may be driven by any of a number of promoters. For example, viral promoters such as the 35S and 19S promoters of CaMV may be used alone or in combination with the omega leader sequence from TMV. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. Such techniques are described in a number of generally available reviews. (See, e.g., Hobbs, S. or Murry, L. E. in *McGraw Hill Yearbook of Science and Technology* (1992) McGraw Hill, New York, N.Y.; pp. 191–196.)

An insect system may also be used to express PPRM. For example, in one such system, *Autographa californica* nuclear polyhedrosis virus (AcNPV) is used as a vector to express foreign genes in *Spodoptera frugiperda* cells or in *Trichoplusia larvae*. The sequences encoding PPRM may be cloned into a non-essential region of the virus, such as the polyhedrin gene, and placed under control of the polyhedrin promoter. Successful insertion of sequences encoding PPRM will render the polyhedrin gene inactive and produce recombinant virus lacking coat protein. The recombinant viruses may then be used to infect, for example, *S. frugiperda* cells or *Trichoplusia larvae* in which PPRM may be expressed. (See, e.g., Engelhard, E. K. et al. (1994) Proc. Nat. Acad. Sci. 91:3224–3227.)

In mammalian host cells, a number of viral-based expression systems may be utilized. In cases where an adenovirus is used as an expression vector, sequences encoding PPRM may be ligated into an adenovirus transcription/translation complex consisting of the late promoter and tripartite leader sequence. Insertion in a non-essential E1 or E3 region of the viral genome may be used to obtain a viable virus which is capable of expressing PPRM in infected host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of about 6 kb to 10 Mb are constructed and delivered via conventional delivery methods (liposomes, polycationic amino polymers, or vesicles) for therapeutic purposes.

Specific initiation signals may also be used to achieve more efficient translation of sequences encoding PPRM. Such signals include the ATG initiation codon and adjacent sequences. In cases where sequences encoding PPRM and its initiation codon and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers appropriate for the particular cell system used. (See, e.g., Scharf, D. et al. (1994) Results Probl. Cell Differ. 20:125–162.)

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding, and/or function. Different host cells which have specific cellular machinery and characteristic mechanisms for post-translational activities (e.g., CHO, HeLa, MDCK, HEK293, and WI38), are available from the American Type Culture Collection (ATCC, Bethesda, Md.) and may be chosen to ensure the correct modification and processing of the foreign protein.

For long term, high yield production of recombinant proteins, stable expression is preferred. For example, cell lines capable of stably expressing PPRM can be transformed using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase genes and adenine phosphoribosyltransferase genes, which can be employed in tk⁻ or apr⁻ cells, respectively. (See, e.g., Wigler, M. et al. (1977) Cell 11:223–232; and Lowy, I. et al. (1980) Cell 22:817–823.) Also, antimetabolite, antibiotic, or herbicide resistance can be used as the basis for selection. For example, dhfr confers resistance to methotrexate; npt confers resistance to the aminoglycosides neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al (1981) J. Mol. Biol. 150:1–14; and Murry, supra.) Additional selectable genes have been described, e.g., trpB, which allows cells to utilize indole in place of tryptophan, or hisD, which allows cells to utilize histinol in place of histidine. (See, e.g., Hartman, S. C. and R. C. Mulligan (1988) Proc. Natl. Acad. Sci. 85:8047–8051.) Visible markers, e.g., anthocyanins, Is glucuronidase and its substrate GUS, luciferase and its substrate luciferin may be used. Green fluorescent proteins (GFP) (Clontech, Palo Alto, Calif) can also be used. These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding PPRM is inserted within a marker gene sequence, transformed cells containing sequences encoding PPRM can be identified by the absence of marker gene function. Alternatively, a marker gene can be placed in tandem with a sequence encoding PPRM under the control of a single promoter. Expression of the marker gene in response to induction or selection usually indicates expression of the tandem gene as well.

Alternatively, host cells which contain the nucleic acid sequence encoding PPRM and express PPRM may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein sequences.

The presence of polynucleotide sequences encoding PPRM can be detected by DNA-DNA or DNA-RNA hybridization or amplification using probes or fragments or fragments of polynucleotides encoding PPRM. Nucleic acid amplification based assays involve the use of oligonucleotides or oligomers based on the sequences encoding PPRM to detect transformants containing DNA or RNA encoding PPRM.

A variety of protocols for detecting and measuring the expression of PPRM, using either polyclonal or monoclonal antibodies specific for the protein, are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on PPRM is preferred, but a competitive binding assay may be employed. These and other assays are well described in the art. (See, e.g., Hampton, R. et al. (1990) *Serological Methods, a Laboratory Manual*, APS Press, St Paul, Minn., Section IV; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding PPRM include oligolabeling, nick translation, end-labeling, or PCR amplification using a labeled nucleotide. Alternatively, the sequences encoding PPRM, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding PPRM may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode PPRM may be designed to contain signal sequences which direct secretion of PPRM through a prokaryotic or eukaryotic cell membrane. Other constructions may be used to join sequences encoding PPRM to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences, such as those specific for Factor XA or enterokinase (Invitrogen, San Diego, Calif), between the purification domain and the PPRM encoding sequence may be used to facilitate purification. One such expression vector provides for expression of a fusion protein containing PPRM and a nucleic acid encoding 6 histidine residues preceding a thioredoxin or an enterokinase cleavage site. The histidine residues facilitate purification on immobilized metal ion affinity chromatography (IMAC). (See, e.g., Porath, J. et al. (1992) Prot. Exp. Purif. 3: 263–281.) The enterokinase cleavage site provides a means for purifying PPRM from the fusion protein. (See, e.g., Kroll, D. J. et al. (1993) DNA Cell Biol. 12:441–453.)

Fragments of PPRM may be produced not only by recombinant production, but also by direct peptide synthesis using solid-phase techniques. (See, e.g., Creighton, supra pp. 55–60.) Protein synthesis may be performed by manual techniques or by automation. Automated synthesis may be achieved, for example, using the Applied Biosystems 431A Peptide Synthesizer (Perkin Elmer). Various fragments of PPRM may be synthesized separately and then combined to produce the full length molecule.

Therapeutics

Chemical and structural homology exists between PPRM of the present invention and enolase-phosphatase from *K. oxytoca* (GI 401712), a protein-tyrosine phosphatase from *C. elegans* (GI 1495338), and a mouse phosphoprotein phosphatase (GI 567040). In addition, PPRM is expressed in tissues associated with cancer and immortalized cell lines, inflammation and the immune response, and in reproductive tissues. Therefore, PPRM appears to play a role in cancer and immune and reproductive disorders.

Therefore, in one embodiment, PPRM or a fragment or derivative thereof may be administered to a subject to treat or prevent a cancer. Such cancers can include, but are not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a vector capable of expressing PPRM or a fragment or derivative thereof may be administered to a subject to treat or prevent a cancer including, but not limited to, those described above.

In a further embodiment, a pharmaceutical composition comprising a substantially purified PPRM in conjunction with a suitable pharmaceutical carrier may be administered to a subject to treat or prevent a cancer including, but not limited to, those provided above.

In still another embodiment, an agonist which modulates the activity of PPRM may be administered to a subject to treat or prevent a cancer including, but not limited to, those listed above.

In another embodiment, PPRM or a fragment or derivative thereof may be administered to a subject to treat or prevent an immune disorder. Such disorders can include, but are not limited to, AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjogren's syndrome, systemic anaphylaxis, systemic lupus erythematosus, systemic sclerosis, ulcerative colitis, Werner syndrome, and complications of cancer, hemodialysis, and extracorporeal circulation, viral, bacterial, fungal, parasitic, protozoal, and helminthic infections, and trauma.

In another embodiment, a vector capable of expressing PPRM or a fragment or derivative thereof may be administered to a subject to treat or prevent an immune disorder including, but not limited to, those described above.

In a further embodiment, a pharmaceutical composition comprising a substantially purified PPRM in conjunction with a suitable pharmaceutical carrier may be administered to a subject to treat or prevent an immune disorder including, but not limited to, those provided above.

In still another embodiment, an agonist which modulates the activity of PPRM may be administered to a subject to treat or prevent an immune disorder including, but not limited to, those listed above.

In another embodiment, PPRM or a fragment or derivative thereof may be administered to a subject to treat or prevent a reproductive disorder. Such disorders can include, but are not limited to, disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, autoimmune disorders, ectopic pregnancy, and teratogenesis; cancer of the breast, uterine fibroids, fibrocystic breast disease, and galactorrhea; disruptions of spermatogenesis, abnormal sperm physiology, cancer of the testis, cancer of the prostate, benign prostatic hyperplasia, prostatitis, Peyronie's disease, carcinoma of the male breast, and gynecomastia.

In another embodiment, a vector capable of expressing PPRM or a fragment or derivative thereof may be administered to a subject to treat or prevent a reproductive disorder including, but not limited to, those described above.

In a further embodiment, a pharmaceutical composition comprising a substantially purified PPRM in conjunction with a suitable pharmaceutical carrier may be administered to a subject to treat or prevent a reproductive disorder including, but not limited to, those provided above.

In still another embodiment, an agonist which modulates the activity of PPRM may be administered to a subject to treat or prevent a reproductive disorder including, but not limited to, those listed above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of PPRM may be produced using methods which are generally known in the art. In particular, purified PPRM may be used to produce antibodies or to screen libraries of pharmaceutical agents to identify those which specifically bind PPRM. Antibodies to PPRM may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with PPRM or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to PPRM have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of PPRM amino acids may be fused with those of another protein, such as KLH, and antibodies to the chimeric molecule may be produced.

Monoclonal antibodies to PPRM may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce PPRM-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; and Winter, G. et al. (1991) Nature 349:293–299.)

Antibody fragments which contain specific binding sites for PPRM may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between PPRM and its specific antibody. A two-site, monoclonal-based immunoassay utilizing monoclonal antibodies reactive to two non-interfering PPRM epitopes is preferred, but a competitive binding assay may also be employed. (Maddox, supra.)

In another embodiment of the invention, the polynucleotides encoding PPRM, or any fragment or complement thereof, may be used for therapeutic purposes. In one aspect, the complement of the polynucleotide encoding PPRM may be used in situations in which it would be desirable to block the transcription of the mRNA. In particular, cells may be transformed with sequences complementary to polynucleotides encoding PPRM. Thus, complementary molecules or fragments may be used to modulate PPRM activity, or to achieve regulation of gene function. Such technology is now well known in the art, and sense or antisense oligonucleotides or larger fragments can be designed from various locations along the coding or control regions of sequences encoding PPRM.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors which will express nucleic acid sequences complementary to the polynucleotides of the gene encoding PPRM. (See, e.g., Sambrook, supra; and Ausubel, supra.)

Genes encoding PPRM can be turned off by transforming a cell or tissue with expression vectors which express high levels of a polynucleotide, or fragment thereof, encoding PPRM. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding PPRM. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding PPRM.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding PPRM. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2'O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of PPRM, antibodies to PPRM, and mimetics, agonists, antagonists, or inhibitors of PPRM. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of PPRM, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example PPRM or fragments thereof, antibodies of PPRM, and agonists, antagonists or inhibitors of PPRM, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of therapeutic to toxic effects is the therapeutic index, and it can be expressed as the $ED_{50}/LD50$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 μg to 100,000 μg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind PPRM may be used for the diagnosis of disorders characterized by expression of PPRM, or in assays to monitor patients being treated with PPRM or agonists, antagonists, or inhibitors of PPRM. Antibodies useful for diagnostic purposes may be prepared in the same manner as described above for therapeutics. Diagnostic assays for PPRM include methods which utilize the antibody and a label to detect PPRM in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring PPRM, including ELISAs, RIAs, and FACS, are known in the art and provide a basis for diagnosing altered or abnormal levels of PPRM expression. Normal or standard values for PPRM expression are established by combining body fluids or cell extracts taken from normal mammalian subjects, preferably human, with antibody to PPRM under conditions suitable for complex formation The amount of standard complex formation may be quantitated by various methods, preferably by photometric means. Quantities of PPRM expressed in subject, control, and disease samples from biopsied tissues are compared with the standard values. Deviation between standard and subject values establishes the parameters for diagnosing disease.

In another embodiment of the invention, the polynucleotides encoding PPRM may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of PPRM may be correlated with disease. The diagnostic assay may be used to determine absence, presence, and excess expression of PPRM, and to monitor regulation of PPRM levels during therapeutic intervention.

In one aspect, hybridization with PCR probes which are capable of detecting polynucleotide sequences, including genomic sequences, encoding PPRM or closely related molecules may be used to identify nucleic acid sequences which encode PPRM. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding PPRM, alleles, or related sequences.

Probes may also be used for the detection of related sequences, and should preferably have at least 50% sequence identity to any of the PPRM encoding sequences. The hybridization probes of the subject invention may be DNA or RNA and may be derived from the sequence of SEQ ID NO:2, SEQ ID NO:4, or SEQ ID NO:6 or from genomic sequences including promoters, enhancers, and introns of the PPRM gene.

Means for producing specific hybridization probes for DNAs encoding PPRM include the cloning of polynucleotide sequences encoding PPRM or PPRM derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding PPRM may be used for the diagnosis of a disorder associated with expression of PPRM. Examples of such a disorder include, but are not limited to, cancers, such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; immune disorders, such as AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjogren's syndrome, systemic anaphylaxis, systemic lupus erythematosus, systemic sclerosis, ulcerative colitis, Werner syndrome, and complications of cancer, hemodialysis, and extracorporeal circulation, viral, bacterial, fungal, parasitic, protozoal, and helminthic infections; and trauma; and reproductive disorders, such as disorders of prolactin production, infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, autoimmune disorders, ectopic pregnancy, and teratogenesis; cancer of the breast, uterine fibroids, fibrocystic breast disease, and galactorrhea; disruptions of spermatogenesis, abnormal sperm physiology, cancer of the testis, cancer of the prostate, benign prostatic hyperplasia, prostatitis, Peyronie's disease, carcinoma of the male breast, and gynecomastia. The polynucleotide sequences encoding PPRM may be used in Southern or northern analysis, dot blot, or other membrane-based technologies; in PCR technologies; in dipstick, pin, and ELISA assays; and in microarrays utilizing fluids or tissues from patients to detect altered PPRM expression. Such qualitative or quantitative methods are well known in the art.

In a particular aspect, the nucleotide sequences encoding PPRM may be useful in assays that detect the presence of associated disorders, particularly those mentioned above. The nucleotide sequences encoding PPRM may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding PPRM in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of PPRM, a normal or standard profile for expression is established. This may be accomplished by combining body fluids or cell extracts taken from normal subjects, either animal or human, with a sequence, or a fragment thereof, encoding PPRM, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding PPRM may involve the use of PCR. These oligomers may be chemically synthesized, generated enzymatically, or produced in vitro. Oligomers will preferably contain a fragment of a polynucleotide encoding PPRM, or a fragment of a polynucleotide complementary to the polynucleotide encoding PPRM, and will be employed under optimized conditions for identification of a specific gene or condition. Oligomers may also be employed under less stringent conditions for detection or quantitation of closely related DNA or RNA sequences.

Methods which may also be used to quantitate the expression of PPRM include radiolabeling or biotinylating nucleotides, coamplification of a control nucleic acid, and interpolating results from standard curves. (See, e.g., Melby, P. C. et al. (1993) J. Immunol. Methods 159:235–244; and Duplaa, C. et al. (1993) Anal. Biochem. 229–236.) The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding PPRM may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995)

in Meyers, R. A. (ed.) *Molecular Biology and Biotechnology*, VCH Publishers New York, N.Y., pp. 965–968.) Examples of genetic map data can be found in various scientific journals or at the Online Mendelian Inheritance in Man (OMIM) site. Correlation between the location of the gene encoding PPRM on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., AT to 11q22–23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, PPRM, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between PPRM and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with PPRM, or fragments thereof, and washed. Bound PPRM is then detected by methods well known in the art. Purified PPRM can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding PPRM specifically compete with a test compound for binding PPRM. In this manner, antibodies can be used to detect the presence of any peptide which shares one or more antigenic determinants with PPRM.

In additional embodiments, the nucleotide sequences which encode PPRM may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. LUNGNOT12 cDNA Library Construction

The LUNGNOT12 cDNA library was constructed from microscopically normal lung tissue obtained from a 78-year-old Caucasian male who had undergone a segmental lung resection following diagnosis of malignant neoplasm of the right upper lobe. The pathology report indicated invasive pulmonary grade 3 adenocarcinoma forming a peripheral mass with associated fibrosis. The fibrosis pleura was puckered, but not invaded. Additionally, the patient exhibited ventricular premature beats and chronic airway obstruction due to extrinsic asthma. The pathology report also indicated a history of cerebrovascular disease, arteriosclerotic vascular disease, thrombophlebitis, malignant neoplastic prostate, and previous tobacco abuse. The patient family history included cerebrovascular disease, arteriosclerotic vascular disease, and Type I diabetes in patient's siblings.

The frozen tissue was homogenized and lysed using a Brinkmann Homogenizer Polytron PT-3000 (Brinkmann Instruments, Westbury, N.J.) in guanidinium isothiocyanate solution. The lysate was centrifuged over a 5.7 M CsCl cushion using an Beckman SW28 rotor in a Beckman L8-70M Ultracentrifuge (Beckman Instruments) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and treated with DNase at 37° C. RNA extraction and precipitation were repeated as before. The mRNA was isolated with the Qiagen Oligotex kit (QIAGEN, Inc., Chatsworth, Calif.) and used to construct the cDNA library.

The MRNA was handled according to the recommended protocols in the SuperScript plasmid system (Catalog #18248-013, GIBCO-BRL). cDNA synthesis was initiated with a NotI-oligo d(T) primer. Double-stranded cDNA was blunted, ligated to EcoRI adaptors, digested with NotI, fractionated on a Sepharose CL4B column (Catalog #275105-01, Pharmacia), and those cDNAs exceeding 400 bp were ligated into the NotI and EcoRI sites of the plasmid pSport I (Catalog #15382-013, GIBCO-BRL). The plasmid pINCY was subsequently transforrned into DH5α™ competent cells (Catalog #18258-012, GIBCO-BRL).

II Isolation and Sequencing of cDNA Clones

Plasmid DNA was released from the cells and purified using the REAL Prep 96 plasmid kit (Catalog #26173, QIAGEN, Inc.). The recommended protocol was employed except for the following changes: 1) the bacteria were cultured in 1 ml of sterile Terrific Broth (Catalog #22711, GLBCOo-BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems; and the reading frame was determined.

III. Homology Searching of cDNA Clones and Their Deduced Proteins

The nucleotide sequences and/or amino acid sequences of the Sequence Listing were used to query sequences in the GenBank, SwissProt, BLOCKS, and Pima II databases.

These databases, which contain previously identified and annotated sequences, were searched for regions of homology using BLAST (Basic Local Alignment Search Tool). (See, e.g., Altschul, S. F. (1993) J. Mol. Evol 36:290–300; and Altschul et al. (1990) J. Mol. Biol. 215:403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms could have been used when dealing with primary sequence patterns and secondary structure gap penalties. (See, e.g., Smith, T. et al. (1992) Protein Engineering 5:35–51.) The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-8}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for homology.

Additionally, sequences identified from cDNA libraries may be analyzed to identify those gene sequences encoding conserved protein motifs using an appropriate analysis program, e.g., the Block 2 Bioanalysis Program (Incyte, Palo Alto, Calif.). This motif analysis program, based on sequence information contained in the Swiss-Prot Database and PROSITE, is a method of determining the function of uncharacterized proteins translated from genomic or cDNA sequences. (See, e.g., Bairoch, A. et al. (1997) Nucleic Acids Res. 25:217–221; and Attwood, T. K. et al. (1997) J. Chem. Inf. Comput. Sci. 37:417–424.) PROSITE may be used to identify common functional or structural domains in divergent proteins. The method is based on weight matrices. Motifs identified by this method are then calibrated against the SWISS-PROT database in order to obtain a measure of the chance distribution of the matches.

In another alternative, Hidden Markov models (HMMs) may be used to find protein domains, each defined by a dataset of proteins known to have a common biological function. (See, e.g., Pearson, W. R. and D. J. Lipman (1988) Proc. Natl. Acad. Sci. 85:2444–2448; and Smith, T. F. and M. S. Waterman (1981) J. Mol. Biol. 147:195–197.) HMMs were initially developed to examine speech recognition patterns, but are now being used in a biological context to analyze protein and nucleic acid sequences as well as to model protein structure. (See, e.g., Krogh, A. et al. (1994) J. Mol. Biol. 235:1501–1531; and Collin, M. et al. (1993) Protein Sci. 2:305–314.) HMMs have a formal probabilistic basis and use position-specific scores for amino acids or nucleotides. The algorithm continues to incorporate information from newly identified sequences to increase its motif analysis capabilities.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, supra, ch. 4 and 16.)

Analogous computer techniques applying BLAST are used to search for identical or related molecules in nucleotide databases such as GenBank or LIFESEQ™ database (Incyte Pharmaceuticals). This analysis is much faster than multiple membrane-based hybridizations. In addition, the sensitivity of the computer search can be modified to determine whether any particular match is categorized as exact or homologous.

The basis of the search is the product score, which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Homologous molecules are usually identified by selecting those which show product scores between 15 and 40, although lower scores may identify related molecules.

The results of northern analysis are reported as a list of libraries in which the transcript encoding PPRM occurs. Abundance and percent abundance are also reported. Abundance directly reflects the number of times a particular transcript is represented in a cDNA library, and percent abundance is abundance divided by the total number of sequences examined in the cDNA library.

V. Extension of PPRM Encoding Polynucleotides

The nucleic acid sequences of Incyte Clones 1359553, 2534680 and 3041794 were used to design oligonucleotide primers for extending partial nucleotide sequences to full length. For each nucleic acid sequence, one primer was synthesized to initiate extension of an antisense polynucleotide, and another was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 (National Biosciences, Plymouth, MN), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (GIBCO/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. PCR was performed using the Peltier Thermal Cycler (PTC200; M.J. Research, Watertown, Mass.), beginning with 40 pmol of each primer and the recommended concentrations of all other components of the kit, with the following parameters:

| | |
|---|---|
| Step 1 | 94° C. for 1 min (initial denaturation) |
| Step 2 | 65° C. for 1 min |
| Step 3 | 68° C. for 6 min |

-continued

| Step 4  | 94° C. for 15 sec                                        |
|---------|----------------------------------------------------------|
| Step 5  | 65° C. for 1 min                                         |
| Step 6  | 68° C. for 7 min                                         |
| Step 7  | Repeat steps 4 through 6 for an additional 15 cycles     |
| Step 8  | 94° C. for 15 sec                                        |
| Step 9  | 65° C. for 1 min                                         |
| Step 10 | 68° C. for 7:15 min                                      |
| Step 11 | Repeat steps 8 through 10 for an additional 12 cycles    |
| Step 12 | 72° C. for 8 min                                         |
| Step 13 | 4° C. (and holding)                                      |

A 5 µl to 10 µl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQuick™ (QIAGEN Inc.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2 to 3 hours, or overnight at 16° C. Competent E. coli cells (in 40 µl of appropriate media) were transformed with 3 µl of ligation mixture and cultured in 80 µl of SOC medium. (See, e.g., Sambrook, supra, Appendix A, p. 2.) After incubation for one hour at 37° C., the E. coli mixture was plated on Luria Bertani (LB) agar (See, e.g., Sambrook, supra, Appendix A, p. 1) containing carbenicillin (2× carb). The following day, several colonies were randomly picked from each plate and cultured in 150 µl of liquid LB/2× Carb medium placed in an individual well of an appropriate commercially-available sterile 96-well microtiter plate. The following day, 5 µl of each overnight culture was transferred into a non-sterile 96-well plate and, after dilution 1:10 with water, 5 µl from each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec                                       |
|--------|---------------------------------------------------------|
| Step 2 | 94° C. for 20 sec                                       |
| Step 3 | 55° C. for 30 sec                                       |
| Step 4 | 72° C. for 90 sec                                       |
| Step 5 | Repeat steps 2 through 4 for an additional 29 cycles    |
| Step 6 | 72° C. for 180 sec                                      |
| Step 7 | 4° C. (and holding)                                     |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequences of SEQ ID NO:2, SEQ ID NO:4, and SEQ ID NO:6 are used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:2 SEQ ID NO:2, SEQ ID NO:4, and SEQ ID NO:6 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 (National Biosciences) and labeled by combining 50 pmol of each oligomer, 250 µCi of $[\gamma\text{-}^{32}P]$ adenosine triphosphate (Amersham, Chicago, Ill.), and T4 polynucleotide kinase (DuPont NEN®, Boston, Mass.). The labeled oligonucleotides are substantially purified using a Sephadex G-25 superfine resin column (Pharmacia & Upjohn, Kalamazoo, Mich.). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba1, or Pvu II (DuPont NEN, Boston, Mass.).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester, N.Y.) is exposed to the blots to film for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE™. Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467–470; and Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the PPRM-encoding sequences, or any parts thereof, are used to detect, decrease, or inhibit expression of naturally occurring PPRM. Although use of oligonucleotides comprising from about 15 to 30 base pairs is described, essentially the same procedure is used with smaller or with larger sequence fragments. Appropriate oligonucleotides are designed using Oligo 4.06 software and the coding sequence of PPRM. To inhibit transcription, a complementary oligonucleotide is designed from the most unique 5' sequence and used to prevent promoter binding to the coding sequence. To inhibit translation, a complementary oligonucleotide is designed to prevent ribosomal binding to the PPRM-encoding transcript.

IX. Expression of PPRM

Expression of PPRM is accomplished by subcloning the cDNA into an appropriate vector and transforming the vector into host cells. This vector contains an appropriate promoter, e.g., β-galactosidase, upstream of the cloning site, operably associated with the cDNA of interest. (See, e.g., Sambrook, supra, pp. 404–433; and Rosenberg, M. et al. (1983) Methods Enzymol. 101: 123–138.)

Induction of an isolated, transformed bacterial strain with isopropyl beta-D-thiogalactopyranoside (IPTG) using standard methods produces a fusion protein which consists of the first 8 residues of β-galactosidase, about 5 to 15 residues of linker, and the full length protein. The signal residues direct the secretion of PPRM into bacterial growth media which can be used directly in the following assay for activity.

X. Demonstration of PPRM Activity

PPRM activity is measured by the hydrolysis of synthetic substrates such as P-nitrophenyl phosphate (PNPP). PPRM is incubated together with PNPP in HEPES buffer pH 7.5, in the presence of 0.1% b-mercaptoethanol at 37° C. for 60 min. The reaction is stopped by the addition of 6 ml of 10 N NaOH and the increase in light absorbance at 410 nm resulting from the hydrolysis of PNPP is measured using a spectrophotometer. The increase in absorbance is proportional to the activity of PPRM in the assay.

XI. Production of PPRM Specific Antibodies

PPRM substantially purified using PAGE electrophoresis (see, e.g., Harrington, M. G. (1990) Methods Enzymol. 182:488–495), or other purification techniques, is used to immunize rabbits and to produce antibodies using standard protocols.

Alternatively, the PPRM amino acid sequence is analyzed using LASERGENE™ software (DNASTAR Inc.) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel supra, ch. 11.)

Typically, oligopeptides 15 residues in length are synthesized using an Applied Biosystems Peptide Synthesizer Model 431A using fmoc-chemistry and coupled to KLH (Sigma, St. Louis, Mo.) by reaction with N-maleimidobenzoyl-N-hydroxysuccinimide ester (MBS) to increase immunogenicity. (See, e.g., Ausubel supra.) Rabbits are immunized with the oligopeptide-KLH complex in complete Freund's adjuvant. Resulting antisera are tested for antipeptide activity, for example, by binding the peptide to plastic, blocking with 1% BSA, reacting with rabbit antisera, washing, and reacting with radio-iodinated goat anti-rabbit IgG.

XII. Purification of Naturally Occurring PPRM Using Specific Antibodies

Naturally occurring or recombinant PPRM is substantially purified by immnunoaffinity chromatography using antibodies specific for PPRM. An immunoaffinity column is constructed by covalently coupling anti-PPRM antibody to an activated chromatographic resin, such as CNBr-activated Sepharose (Pharmacia & Upjohn). After the coupling, the resin is blocked and washed according to the manufacturer's instructions.

Media containing PPRM are passed over the immunoaffinity column, and the column is washed under conditions that allow the preferential absorbance of PPRM (e.g., high ionic strength buffers in the presence of detergent). The column is eluted under conditions that disrupt antibody/PPRM binding (e.g., a buffer of pH 2 to pH 3, or a high concentration of a chaotrope, such as urea or thiocyanate ion), and PPRM is collected.

XIII. Identification of Molecules Which Interact with PPRM

PPRM, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled PPRM, washed, and any wells with labeled PPRM complex are assayed. Data obtained using different concentrations of PPRM are used to calculate values for the number, affinity, and association of PPRM with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide encoding a polypeptide selected from group consisting of: SEQ ID NO: 1, SEQ ID NO: 3, and SEQ ID NO: 5.

2. An isolated and purified polynucleotide of claim 1 comprising a nucleic acid sequence selected from the group consisting of: SEQ ID NO: 2, SEQ ID NO: 4, and SEQ ID NO: 6, wherein the polynucleotide encodes a polypeptide which hydrolyzes P-nitrophenyl phosphate.

3. An isolated and purified polynucleotide which hybridizes under stringent conditions to the polynucleotide of claim 2 wherein stringent conditions comprise wash conditions of 0.1× SSC, 0.5% SDS, at 68° C., wherein the polynucleotide encodes a polypeptide which hydrolyzes P-nitrophenyl phosphate.

4. An isolated and purified polynucleotide having a sequence which is fully complementary to the polynucleotide sequence of claim 2.

5. An isolated and purified polynucleotide of claim 2 selected from the group consisting of SEQ ID NO:2, SEQ ID NO:4, and SEQ ID NO:6.

6. An isolated and purified polynucleotide having at least 90% identity to the polynucleotide of claim 5, wherein the polynucleotide encodes a polypeptide which hydrolyzes P-nitrophenyl phosphate.

7. An isolated and purified polynucleotide having a sequence which is fully complementary to the polynucleotide of claim 5.

8. An expression vector containing the polynucleotide of claim 2.

9. A host cell containing the expression vector of claim 8.

10. A method for producing a polypeptide comprising an amino acid sequence selected from the group consisting of SEQ ID NO:1, SEQ ID NO:3, and SEQ ID NO:5, the method comprising the steps of:
   a) culturing the host cell of claim 9 under conditions suitable for the expression of the polypeptide; and
   b) recovering the polypeptide from the host cell culture.

11. A method for detecting a polynucleotide encoding a polypeptide comprising an amino acid sequence selected from the group consisting of SEQ ID NO: 1, SEQ ID NO:3, and SEQ ID NO:5 the method comprising the steps of:
   (a) hybridizing the polynucleotide of claim 2 to at least one of the nucleic acids of the biological sample, wherein hybridization conditions comprise wash conditions of 0.1× SSC, 0.5% SDS, at 68° C., thereby forming a hybridization complex; and
   (b) detecting the hybridization complex, wherein the presence of the hybridization complex correlates with the presence of the polynucleotide encoding the polypeptide in the biological sample.

12. The method of claim 11 wherein the nucleic acids of the biological sample are amplified by the polymerase chain reaction prior to the hybridizing step.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 303 amino acids
      (B) TYPE: amino acid
      (C) STRANDEDNESS: single
      (D) TOPOLOGY: linear (xi) SEQUENCE DESCRIPTION: SEQ ID NO:1:

```
Met Lys Gly Lys Glu Glu Lys Glu Gly Gly Ala Arg Leu Gly Ala Gly
  1               5                  10                  15
Gly Gly Ser Pro Glu Lys Ser Pro Ser Ala Gln Glu Leu Lys Glu Gln
             20                  25                  30
Gly Asn Arg Leu Phe Val Gly Arg Lys Tyr Pro Glu Ala Ala Cys
             35                  40                  45
Tyr Gly Arg Ala Ile Thr Arg Asn Pro Leu Val Ala Val Tyr Tyr Thr
 50                  55                  60
Asn Arg Ala Leu Cys Tyr Leu Lys Met Gln Gln His Glu Gln Ala Leu
 65                  70                  75                  80
Ala Asp Cys Arg Arg Ala Leu Glu Leu Asp Gly Gln Ser Val Lys Ala
                 85                  90                  95
His Phe Phe Leu Gly Gln Cys Gln Leu Glu Met Glu Ser Tyr Asp Glu
                100                 105                 110
Ala Ile Ala Asn Leu Gln Arg Ala Tyr Ser Leu Ala Lys Glu Gln Arg
             115                 120                 125
Leu Asn Phe Gly Asp Asp Ile Pro Ser Ala Leu Arg Ile Ala Lys Lys
130                 135                 140
Lys Arg Trp Asn Ser Ile Glu Glu Arg Arg Ile His Gln Glu Ser Glu
145                 150                 155                 160
Leu His Ser Tyr Leu Ser Arg Leu Ile Ala Ala Glu Arg Glu Arg Glu
                165                 170                 175
Leu Glu Glu Cys Gln Arg Asn His Glu Gly Asp Glu Asp Asp Ser His
                180                 185                 190
Val Arg Ala Gln Gln Ala Cys Ile Glu Ala Lys His Asp Lys Tyr Met
            195                 200                 205
Ala Asp Met Asp Glu Leu Phe Ser Gln Val Asp Glu Lys Arg Lys Lys
210                 215                 220
Arg Asp Ile Pro Asp Tyr Leu Cys Gly Lys Ile Ser Phe Glu Leu Met
225                 230                 235                 240
Arg Glu Pro Cys Ile Thr Pro Ser Gly Ile Thr Tyr Asp Arg Lys Asp
                245                 250                 255
Ile Glu Glu His Leu Gln Arg Val Gly His Phe Asp Pro Val Thr Arg
            260                 265                 270
Ser Pro Leu Thr Gln Glu Gln Leu Ile Pro Asn Leu Ala Met Lys Glu
            275                 280                 285
Val Ile Asp Ala Phe Ile Ser Glu Asn Gly Trp Val Glu Asp Tyr
290                 295                 300
```

(2) INFORMATION FOR SEQ ID NO:2:

(i) SEQUENCE CHARACTERISTICS:
        (A) LENGTH: 1335 base pairs
        (B) TYPE: nucleic acid
        (C) STRANDEDNESS: single
        (D) TOPOLOGY: linear (vii) IMMEDIATE SOURCE:
        (A) LIBRARY: LUNGNOT12
        (B) CLONE: 1359553

(xi) SEQUENCE DESCRIPTION: SEQ ID NO:2:

```
ATCGCGGGCT CGGGCTGCGG GGCTCCGGCT GCGGGCGCTG GGCCGCGAGG CGCGGAGCTT      60

GGGAGCGGAG CCCAGGCCGT GCCGCGCGGC GCCATGAAGG GCAAGGAGGA GAAGGAGGGC     120

GGCGCACGGC TGGGCGCTGG CGGCGGAAGC CCCGAGAAGA GCCCGAGCGC GCAGGAGCTC     180
```

-continued

```
AAGGAGCAGG GCAATCGTCT GTTCGTGGGC CGAAAGTACC CGGAGGCGGC GGCCTGCTAC      240

GGCCGCGCGA TCACCCGGAA CCCGCTGGTG GCCGTGTATT ACACCAACCG GGCCTTGTGC      300

TACCTGAAGA TGCAGCAGCA CGAGCAGGCC CTGGCCGACT GCCGGCGCGC CCTGGAGCTG      360

GACGGGCAGT CTGTGAAGGC GCACTTCTTC CTGGGGCAGT GCCAGCTGGA GATGGAGAGC      420

TATGATGAGG CCATCGCCAA TCTGCAGCGA GCTTACAGCC TGGCCAAGGA GCAGCGGCTG      480

AACTTCGGGG ACGACATCCC CAGCGCTCTT CGAATCGCGA AGAAGAAGCG CTGGAACAGC      540

ATTGAGGAGC GGCGCATCCA CCAGGAGAGC GAGCTGCACT CCTACCTCTC CAGGCTCATT      600

GCCGCGGAGC GTGAGAGGGA GCTGGAAGAG TGCCAGCGAA ACCACGAGGG TGATGAGGAC      660

GACAGCCACG TCCGGGCCCA GCAGGCCTGC ATTGAGGCCA AGCACGACAA GTACATGGCG      720

GACATGGACG AGCTTTTTTC TCAGGTGGAT GAGAAGAGGA AGAAGCGAGA CATCCCCGAC      780

TACCTGTGTG GCAAGATCAG CTTTGAGCTG ATGCGGGAGC CGTGCATCAC GCCCAGTGGC      840

ATCACCTACG ACCGCAAGGA CATCGAGGAG CACCTGCAGC GTGTGGGTCA TTTTGACCCC      900

GTGACCCGGA GCCCCCTGAC CCAGGAACAG CTCATCCCCA ACTTGGCTAT GAAGGAGGTT      960

ATTGACGCAT TCATCTCTGA GAATGGCTGG GTGGAGGACT ACTGAGGTTC CCTGCCCTAC     1020

CTGGCGTCCT GGTCCAGGGG AGCCCTGGGC AGAAGCCCCC GGCCCCTATA CATAGTTTAT     1080

GTTCCTGGCC ACCCCGACCG CTTCCCCCAA GTTCTGCTGT TGGACTCTGG ACTGTTTCCC     1140

CTCTCAGCAT CGCTTTTGCT GGGCCGTGAT CGTCCCCCTT TGTGGGCTGG AAAAGCAGGT     1200

GAGGGTGGGC TGGGCTGAGG CCATTGCCGC CACTATCTGT GTAATAAAAT CCGTGAGCAC     1260

GAGGTGGGAC GTGCTGGTGT GTGACCGGCA GTCCTGCCAG CTGTTTTGGC TAGCCGAGGA     1320

AGGTGGAGAT GAAGA                                                     1335
```

(2) INFORMATION FOR SEQ ID NO:3:

(i) SEQUENCE CHARACTERISTICS:
        (A) LENGTH: 261 amino acids
        (B) TYPE: amino acid
        (C) STRANDEDNESS: single
        (D) TOPOLOGY: linear (vii) IMMEDIATE SOURCE:
        (A) LIBRARY: BRAINOT18
        (B) CLONE: 2534680

(xi) SEQUENCE DESCRIPTION: SEQ ID NO:3:

```
Met Val Val Leu Ser Val Pro Ala Glu Val Thr Val Ile Leu Leu Asp
 1               5                  10                  15

Ile Glu Gly Thr Thr Thr Pro Ile Ala Phe Val Lys Asp Ile Leu Phe
            20                  25                  30

Pro Tyr Ile Glu Glu Asn Val Lys Glu Tyr Leu Gln Thr His Trp Glu
        35                  40                  45

Glu Glu Glu Cys Gln Gln Asp Val Ser Leu Leu Arg Lys Gln Ala Glu
    50                  55                  60

Glu Asp Ala His Leu Asp Gly Ala Val Pro Ile Pro Ala Ala Ser Gly
65                  70                  75                  80

Asn Gly Val Asp Asp Leu Gln Gln Met Ile Gln Ala Val Val Asp Asn
                85                  90                  95

Val Cys Trp Gln Met Ser Leu Asp Arg Lys Thr Thr Ala Leu Lys Gln
            100                 105                 110

Leu Gln Gly His Met Trp Arg Ala Ala Phe Thr Ala Gly Arg Met Lys
        115                 120                 125
```

```
Ala Glu Phe Phe Ala Asp Val Val Pro Ala Val Arg Lys Trp Arg Glu
    130                 135                 140
Ala Gly Met Lys Val Tyr Ile Tyr Ser Ser Gly Ser Val Glu Ala Gln
145                 150                 155                 160
Lys Leu Leu Phe Gly His Ser Thr Glu Gly Asp Ile Leu Glu Leu Val
                165                 170                 175
Asp Gly His Phe Asp Thr Lys Ile Gly His Lys Val Glu Ser Glu Ser
            180                 185                 190
Tyr Arg Lys Ile Ala Asp Ser Ile Gly Cys Ser Thr Asn Asn Ile Leu
        195                 200                 205
Phe Leu Thr Asp Val Thr Arg Glu Ala Ser Ala Ala Glu Glu Ala Asp
    210                 215                 220
Val His Val Ala Val Val Arg Pro Gly Asn Ala Gly Leu Thr Asp
225                 230                 235                 240
Asp Glu Lys Thr Tyr Tyr Ser Leu Ile Thr Ser Phe Ser Glu Leu Tyr
                245                 250                 255
Leu Pro Ser Ser Thr
            260
```

(2) INFORMATION FOR SEQ ID NO:4:

(i) SEQUENCE CHARACTERISTICS:
        (A) LENGTH: 1970 base pairs
        (B) TYPE: nucleic acid
        (C) STRANDEDNESS: single
        (D) TOPOLOGY: linear (vii) IMMEDIATE SOURCE:
        (A) LIBRARY: BRAINOT18
        (B) CLONE: 2534680

(xi) SEQUENCE DESCRIPTION: SEQ ID NO:4:

```
GGGCGGCCGC CTTTTCCAGT TCCAGGTGTG CAGAAGTGTC CTCTCCCCAC GCGCGGCGGG      60
CTGCACTTGG TCGCTGGCTC CGAGATCGCG CGGGGCCGCC GGAAGCCCAA GACGGTACCG     120
GGGGCCGCAG CCGCAGCCGG CGCCGCCCTC CGCCCTCCCC AACAGCAGGC CGAGTCCCGT     180
AGCATCCGGT AGGGAAATGG TCGTGCTTTC GGTCCCCGCC GAAGTCACCG TGATCCTGTT     240
AGATATCGAA GGTACCACAA CCCCGATTGC TTTCGTGAAG GACATTTTAT TTCCTTACAT     300
CGAAGAAAAT GTTAAAGAGT ATCTGCAGAC ACATTGGGAA GAAGAGGAGT GCCAGCAGGA     360
TGTCAGTCTT TTGAGGAAAC AGGCTGAAGA GGACGCCCAC CTGGATGGGG CTGTTCCTAT     420
CCCTGCAGCA TCTGGGAATG GAGTGGATGA TCTGCAACAG ATGATCCAGG CCGTGGTAGA     480
TAATGTGTGC TGGCAGATGT CCCTGGATCG AAAGACCACT GCACTCAAAC AGCTGCAGGG     540
CCACATGTGG AGGGCGGCAT TCACAGCTGG GCGCATGAAA GCAGAGTTCT TTGCAGATGT     600
AGTTCCAGCA GTCAGGAAGT GGAGAGAGGC CGGAATGAAG GTGTACATCT ATTCCTCAGG     660
GAGTGTGGAG GCACAGAAAC TGTTATTCGG GCATTCTACG GAGGGAGATA TTCTTGAGCT     720
TGTTGATGGT CACTTTGATA CCAAGATTGG ACACAAAGTA GAGAGTGAAA GTTACCGAAA     780
GATTGCAGAC AGCATTGGGT GCTCAACCAA CAACATTTTG TTTCTGACAG ATGTTACTCG     840
AGAGGCCAGT GCTGCTGAGG AAGCAGATGT GCACGTAGCT GTGGTGGTGA GACCAGGCAA     900
CGCAGGATTA ACAGATGATG AGAAGACTTA CTACAGCCTC ATCACATCCT TCAGTGAACT     960
ATACCTGCCT TCCTCAACCT AGAGAAGGGT TGTTAAGGCA GACCGCCCTG TTCCCCAGAG    1020
TTGTCCCTGT AGTGTCTAGG TTTATTCTAA TGGTAAAAGT AACTTACTTA AAAAACATAT    1080
GTACACATAT GTATGCAAGT ATGTATATAT GTGTATGCTC AGATTAACTT CCATAGGTAC    1140
```

-continued

```
ATAAGTGAAA GAAGTCTCAG TTCAGTGAAC ACAAAACTTA TTTAAAGATG CTTTATATGT    1200

AGAAATTGTT TCAAATCATA CTCTAACCCT TAGTGAGGGC AAAGTGTAGT TGGTAGAAGA    1260

AATTGCTAAA TACCTATCTA ATGTGCTATG TTTATCAAAT CGTGTACTAA AATGGAAAGC    1320

TAGTTTTGAG AAATTATTCA GAAGCCTTGT TATTTTAAAA ATGAAATATT TCAAAGACTG    1380

AATATTTTCA AAGAAAATGA ATAATTCATT GCCCTTGTGA TTTAGAAGAT TATAACAGCT    1440

GTATTTCATA TTTGCCTCCT TATATATATC AAAGACCAAG GTATTTCCTT CTGCTTCAAA    1500

AGAACAAAAT TGGGAAAGAA AACTCACTTG AGTCTTGATC AAACAAGTGT CTTTTACTTA    1560

AGAAGAAACT TGGTAATCAT TGTGGCACCC ACAGCAAGCA GTTGCCTTAC CAGTGAAAAA    1620

GGTGCACTGA GGTAACATCT AAAACAGAGA TGTGGTTCTT AATGTTTAAC AGAACAGTTC    1680

TAATCCTGCC ACGTGTTATC ATTATAGATT TTATAGTTGC CTTTCTAACT ACTTAGCACA    1740

GTTTGAGAAT ACGTTAATTG CTATTTACTA TTTAAAAAGT TTTACTGAAA TCAGTCCATA    1800

ACATTAAGAT GAGCCCTAAT ATGTAAGATT TTCCTCTGGA ATGGATGTGA GAAATGTAAA    1860

TTTTATAACA GCAGTATTTA TCCTGGTTTA ATTCTAATAC GATGTCATGT TAATTTCATG    1920

TTGTGATTAA TAAAAGCATT TTTTCTTCAC TCAAAAAAAA AACGGTCGAG              1970
```

(2) INFORMATION FOR SEQ ID NO:5:

(i) SEQUENCE CHARACTERISTICS:
        (A) LENGTH: 198 amino acids
        (B) TYPE: amino acid
        (C) STRANDEDNESS: single
        (D) TOPOLOGY: linear (vii) IMMEDIATE SOURCE:
        (A) LIBRARY: BRSTNOT16
        (B) CLONE: 3041794

(xi) SEQUENCE DESCRIPTION: SEQ ID NO:5:

```
Met Ser Ser Arg Gly His Ser Thr Leu Pro Arg Thr Leu Met Ala Pro
  1               5                  10                  15

Arg Met Ile Ser Glu Gly Asp Ile Gly Ile Ala Gln Ile Thr Ser
             20                  25                  30

Ser Leu Phe Leu Gly Arg Gly Ser Val Ala Ser Asn Arg His Leu Leu
         35                  40                  45

Gln Ala Arg Gly Ile Thr Cys Ile Val Asn Ala Thr Ile Glu Ile Pro
 50                  55                  60

Asn Phe Asn Trp Pro Gln Phe Glu Tyr Val Lys Val Pro Leu Ala Asp
 65                  70                  75                  80

Met Pro His Ala Pro Ile Gly Leu Tyr Phe Asp Thr Val Ala Asp Lys
                 85                  90                  95

Ile His Ser Val Ser Arg Lys His Gly Ala Thr Leu Val His Cys Ala
                100                 105                 110

Ala Gly Val Ser Arg Ser Ala Thr Leu Cys Ile Ala Tyr Leu Met Lys
            115                 120                 125

Phe His Asn Val Cys Leu Leu Glu Ala Tyr Asn Trp Val Lys Ala Arg
        130                 135                 140

Arg Pro Val Ile Arg Pro Asn Val Gly Phe Trp Arg Gln Leu Ile Asp
145                 150                 155                 160

Tyr Glu Arg Gln Leu Phe Gly Lys Ser Thr Val Lys Met Val Gln Thr
                165                 170                 175

Pro Tyr Gly Ile Val Pro Asp Val Tyr Glu Lys Glu Ser Arg His Leu
            180                 185                 190
```

```
Met Pro Tyr Trp Gly Ile
        195
```

(2) INFORMATION FOR SEQ ID NO:6:

(i) SEQUENCE CHARACTERISTICS:
        (A) LENGTH: 1729 base pairs
        (B) TYPE: nucleic acid
        (C) STRANDEDNESS: single
        (D) TOPOLOGY: linear (vii) IMMEDIATE SOURCE:
        (A) LIBRARY: BRSTNOT16
        (B) CLONE: 3041794

(xi) SEQUENCE DESCRIPTION: SEQ ID NO:6:

```
GGACAATCAC CAGAGAGCTG AATTTTACAT TGATTTCACA TGTTTGTGTC TTAGGTGACT      60
TTTCCCAACT GTTAATTGAT AGAAAATGAT TTGTCTGTAT CCTTGAAAGA TTGTACTGTA     120
TTATTTAAAA AAAAACCCTC TAATCTTCCC ATTTGACAAA TGTGACAGAA GGCTGTGATG     180
AATCAGTAGC ATTTAAAGTA CTGACACATA CCTGTATTTT GCAGCGCGCG CGGCGCCCAG     240
CCCGCAGAAG CCGGTGGCCG CGCAGGAGGA CGGAGCCCTA ACCGCAACCC GCGCCGCGCC     300
GCGCCGCGCC GATTTGATTT GTATCCACTG TCACCAGCAC TGCTCACTTA GGACTTTCTG     360
GATCCAGACC CAGGCAGCGC ACACTGGACT CTTGAGGAAG AAGGAGACTC TAATTTTGGA     420
TTCCTTGGTG GAGGAAAATA AAACACTCTG GTCTTGCCGC CAACGATGCA AGTGTGACTG     480
CTGGCGTCTT CATGAGCTCC AGAGGTCACA GCACGCTACC AAGGACTCTC ATGGCCCCTC     540
GGATGATTTC CGAGGGAGAC ATAGGAGGCA TTGCTCAAAT CACCTCCTCT CTATTCCTGG     600
GCAGAGGCAG TGTGGCCTCC AATCGGCACC TCCTCCAGGC TCGTGGCATC ACCTGCATTG     660
TTAATGCTAC CATTGAGATC CCTAATTTCA ACTGGCCCCA ATTTGAGTAT GTTAAAGTGC     720
CTCTGGCTGA CATGCCGCAT GCCCCCATTG GACTGTACTT TGACACCGTG GCTGACAAGA     780
TCCACAGTGT GAGCAGGAAG CACGGGGCCA CCTTGGTGCA CTGTGCTGCA GGGGTGAGCC     840
GCTCAGCCAC GCTGTGTATC GCGTACCTGA TGAAATTCCA CAACGTGTGC CTGCTGGAGG     900
CGTACAACTG GGTGAAAGCC CGGCGACCTG TCATCAGGCC CAACGTAGGC TTCTGGAGGC     960
AACTGATAGA CTACGAGCGC CAGCTCTTTG GGAAGTCGAC AGTTAAAATG GTACAGACAC    1020
CTTATGGCAT AGTTCCCGAC GTCTATGAGA AGGAGTCCCG ACACCTGATG CCTTACTGGG    1080
GGATTTAGTG CCACTGAAGC CTGCGTCAGC AGCCCGAGCG GGGCCGGCAT CTGCTCCCCG    1140
CCGTCTGCTC CCTCTCCACT CTCTTCTCAA ATGGCTGACT TCTGGTTCTC CCTCAAGTGT    1200
TTTTTACACT GGGTGTTCAA ATTTATTTTA AGAGATAGGG AGGGAGGGGA CATAAAGGGA    1260
ATGCATACAT TGCTAGTCAC ATTTTTAAAA TTAACATTTT GGAATAGTGT TTATGGAAAT    1320
CTTTAGCTTT TAATCATTTT TACCAATTTG AACAGTTTAA TAAACTGGTT CTGCTCTCTT    1380
CTGAATCTCA TGCCTTTGGC ACCTTGGTAG GTGCAGGAGG AGCTCAGTGC AAAAATCACT    1440
TTGGGGCCTC ATTAACCCTT TAGAGACAAG CTTTGCCCCA GGCTGCGGAC CAGACAGATG    1500
CTTAGGGAAG GTTGATAACC AGCTTCAGTC TCTACTGGAT TAGCCCTACT CTTTCCTTTC    1560
CCCTCCATTA TTTAGTGACT CTGTAAGTAA GTTAAATACA CCCTTATTAT TTAGCTGTTA    1620
AGTAACTATA ATGAAATCTG CTGCAAAATC TCTCTTGGAA TCCATGTGCC CAGGATTATA    1680
TTAGCATTAT TTTTAATAAA TCTATATGCT TAACATATTA AAAAAAAA                 1729
```

(2) INFORMATION FOR SEQ ID NO:7:

(i) SEQUENCE CHARACTERISTICS:
   (A) LENGTH: 229 amino acids
   (B) TYPE: amino acid
   (C) STRANDEDNESS: single
   (D) TOPOLOGY: linear (vii) IMMEDIATE SOURCE:
   (A) LIBRARY: GenBank
   (B) CLONE: 401712

(xi) SEQUENCE DESCRIPTION: SEQ ID NO:7:

```
Met Ile Arg Ala Ile Val Thr Asp Ile Glu Gly Thr Thr Ser Asp Ile
1               5                   10                  15

Arg Phe Val His Asn Val Leu Phe Pro Tyr Ala Arg Glu Arg Leu Ala
            20                  25                  30

Gly Phe Val Thr Ala Gln Gln Phe Val Glu Pro Val Lys Thr Ile Leu
            35                  40                  45

Asp Asn Leu Arg Glu Glu Ile Ala Gln Pro Ala Ala Gly Ala Glu Glu
50                  55                  60

Leu Ile Ala Thr Leu Phe Ala Phe Met Asp Glu Asp Arg Lys Ser Thr
65                  70                  75                  80

Ala Leu Lys Ala Leu Gln Gly Ile Ile Trp Arg Asp Gly Tyr Val His
            85                  90                  95

Gly Asp Phe Thr Gly His Leu Tyr Pro Asp Val Leu Pro Ala Leu Glu
            100                 105                 110

Lys Trp Lys Ser Gln Gly Ile Asp Leu Tyr Val Tyr Ser Ser Gly Ser
            115                 120                 125

Val Ala Ala Gln Lys Leu Leu Phe Gly Tyr Ser Asp Glu Gly Asp Ile
130                 135                 140

Thr His Leu Phe Asn Gly Tyr Phe Asp Thr Leu Val Gly Ala Lys Arg
145                 150                 155                 160

Glu Ala Gln Ser Tyr Arg Asn Ile Ala Glu Gln Leu Gly Gln Pro Pro
            165                 170                 175

Ala Ala Ile Leu Phe Leu Ser Asp Ile His Gln Glu Leu Asp Ala Ala
            180                 185                 190

Glu Glu Ala Gly Phe Arg Thr Leu Gln Leu Val Arg Gly Asp Arg Asp
            195                 200                 205

Pro Ala Ser His His Pro Gln Val Gln Arg Phe Asp Asp Ile His Pro
210                 215                 220

Glu Gln Ile Pro Ala
225
```

(2) INFORMATION FOR SEQ ID NO:8:

(i) SEQUENCE CHARACTERISTICS:
   (A) LENGTH: 226 amino acids
   (B) TYPE: amino acid
   (C) STRANDEDNESS: single
   (D) TOPOLOGY: linear (vii) IMMEDIATE SOURCE:
   (A) LIBRARY: GenBank
   (B) CLONE: 1495338

(xi) SEQUENCE DESCRIPTION: SEQ ID NO:8:

```
Met Thr Leu Ser Phe Arg Val Asn Pro Glu Tyr Ala Ala Met Ser Glu
1               5                   10                  15

Ile Val Pro Gly Leu Phe Ile Cys Gly Val Ser Ala Leu Ser Lys Asp
            20                  25                  30
```

```
Glu Met Lys Lys His Lys Ile Thr His Ile Ile Asn Ala Thr Thr Glu
         35                  40                  45

Val Pro Asn Leu Arg Ser Leu Gly Asp Ile Gln Arg Thr Lys Leu Trp
     50                  55                  60

Leu Glu Asp Thr Pro Gln Thr Tyr Ile Tyr Pro His Leu Glu Leu Gln
 65                  70                  75                  80

Ser Asp Gln Ile Gln Ala Leu Ile Ala Asp Gly Gly Lys Val Leu Val
                 85                  90                  95

His Cys Val Ala Gly Val Ser Arg Ser Ala Ser Ile Cys Leu Ala Phe
                100                 105                 110

Leu Leu Lys Tyr Arg Cys Arg Asn Leu Arg Glu Ala Tyr His Leu Met
            115                 120                 125

Lys Ser Lys Arg Ser Met Val Arg Pro Asn Leu Gly Phe Trp Arg Gln
        130                 135                 140

Leu Ile Ala Tyr Glu Gln Asn Val Lys Glu Asn Ala Gly Ser Val Arg
145                 150                 155                 160

Leu Val Arg Asp Glu Ala Gln Pro Glu Gln Leu Leu Pro Asp Val Tyr
                165                 170                 175

Leu Asn Ile Ala Ile Pro Ala Arg Pro Ala Ser Pro Glu Gln Asp Pro
                180                 185                 190

Asn Met Ile Pro Asp Glu Pro Arg Glu Arg Arg Asn Ser Gly Phe Lys
            195                 200                 205

Ser Lys Phe Arg Pro Val Leu Glu Pro Val Met Glu Met Ala Glu Ala
        210                 215                 220

Val Cys
225

(2) INFORMATION FOR SEQ ID NO:9:

(i) SEQUENCE CHARACTERISTICS:
        (A) LENGTH: 144 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 567040

(xi) SEQUENCE DESCRIPTION: SEQ ID NO:9:

Ala Glu Thr Pro Arg Asp Glu Pro Pro Ala Asp Gly Thr Leu Lys Arg
 1               5                  10                  15

Ala Glu Glu Leu Lys Thr Gln Ala Asn Asp Tyr Phe Lys Ala Lys Asp
                20                  25                  30

Tyr Glu Asn Ala Ile Lys Phe Tyr Ser Gln Ala Ile Glu Leu Asn Pro
            35                  40                  45

Gly Asn Ala Ile Tyr Tyr Gly Asn Arg Ser Leu Ala Tyr Leu Arg Thr
        50                  55                  60

Glu Cys Tyr Gly Tyr Ala Leu Gly Asp Ala Thr Arg Ala Ile Glu Leu
65                  70                  75                  80

Asp Lys Lys Tyr Ile Lys Gly Tyr Tyr Arg Arg Ala Ala Ser Asn Met
                85                  90                  95

Ala Leu Gly Lys Phe Arg Ala Ala Leu Arg Asp Tyr Glu Thr Val Val
                100                 105                 110
```

-continued

```
Lys Val Lys Pro Asn Asp Lys Asp Ala Lys Met Lys Tyr Gln Glu Cys
        115                 120                 125

Ser Lys Ile Val Lys Gln Lys Ala Phe Glu Arg Ala Ile Ala Gly Gly
        130                 135                 140
```